US011096620B1

(12) United States Patent
Seidman et al.

(10) Patent No.: US 11,096,620 B1
(45) Date of Patent: Aug. 24, 2021

(54) WEARABLE MODULE ASSEMBLIES FOR AN OPTICAL MEASUREMENT SYSTEM

(71) Applicant: HI LLC, Los Angeles, CA (US)

(72) Inventors: Scott Jeremy Seidman, Glenview, IL (US); Ryan Field, Culver City, CA (US); Husam Katnani, Braintree, MA (US); Katherine Perdue, Los Angeles, CA (US); Isai Olvera, San Jose, CA (US); Alan Millman, Rancho Palos Verdes, CA (US); Zachary Phillip Sheldon, Venice, CA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 17/176,460

(22) Filed: Feb. 16, 2021

Related U.S. Application Data

(60) Provisional application No. 63/081,754, filed on Sep. 22, 2020, provisional application No. 62/992,550,
(Continued)

(51) Int. Cl.
*A61B 5/00* (2006.01)
*G01N 33/483* (2006.01)

(52) U.S. Cl.
CPC .......... *A61B 5/4064* (2013.01); *A61B 5/0075* (2013.01); *A61B 5/0082* (2013.01);
(Continued)

(58) Field of Classification Search
CPC ... A61B 5/4064; A61B 5/6803; A61B 5/0082; A61B 5/0075; A61B 5/1455;
(Continued)

(56) References Cited

U.S. PATENT DOCUMENTS

| 4,018,534 A | 4/1977 | Thorn et al. |
| 4,207,892 A | 6/1980 | Binder |

(Continued)

FOREIGN PATENT DOCUMENTS

| EP | 2294973 | 3/2011 |
| EP | 3419168 | 12/2018 |

(Continued)

OTHER PUBLICATIONS

International Search Report and Written Opinion received in International Application No. PCT/2020/027537, dated Sep. 7, 2020.
(Continued)

*Primary Examiner* — Chu Chuan Liu
(74) *Attorney, Agent, or Firm* — ALG Intellectual Property, LLC

(57) ABSTRACT

An optical measurement system includes a wearable module assembly configured to be worn on a body of a user. The wearable module assembly includes a plurality of wearable modules and a connecting assembly. Each wearable module includes a light source configured to emit a light pulse toward a target within the body of the user and a plurality of detectors configured to receive photons included in the light pulse after the photons are scattered by the target. The connecting assembly physically and flexibly connects the plurality of wearable modules such that the wearable module assembly is conformable to a three-dimensional (3D) surface of the body of the user when the wearable module assembly is worn on the body of the user.

26 Claims, 22 Drawing Sheets

Related U.S. Application Data filed on Mar. 20, 2020, provisional application No. 62/979,866, filed on Feb. 21, 2020.

(52) U.S. Cl.
CPC ....... *A61B 5/6803* (2013.01); *G01N 33/4833* (2013.01); *A61B 2562/046* (2013.01); *A61B 2562/164* (2013.01); *A61B 2562/225* (2013.01)

(58) Field of Classification Search
CPC ............ A61B 5/14551; A61B 5/14552; A61B 5/14532; A61B 5/14553; A61B 5/14556; A61B 2562/164; A61B 2562/225; A61B 2562/046

See application file for complete search history.

(56) References Cited

U.S. PATENT DOCUMENTS

| | | |
|---|---|---|
| 4,281,645 A | 8/1981 | Jobsis |
| 4,515,165 A | 5/1985 | Carroll |
| 4,655,225 A | 4/1987 | Dahne et al. |
| 4,963,727 A | 10/1990 | Cova |
| 5,090,415 A | 2/1992 | Yamashita |
| 5,853,370 A | 12/1998 | Chance et al. |
| 5,929,982 A | 7/1999 | Anderson |
| 6,163,715 A | 12/2000 | Larsen et al. |
| 6,240,309 B1 | 5/2001 | Yamashita et al. |
| 6,384,663 B2 | 5/2002 | Coda et al. |
| 6,541,752 B2 | 4/2003 | Zappa et al. |
| 6,683,294 B1 | 1/2004 | Herbert et al. |
| 6,992,772 B2 | 1/2006 | Block |
| 7,095,491 B2 | 8/2006 | Forstner et al. |
| 7,356,365 B2 | 4/2008 | Schurman |
| 7,507,596 B2 | 3/2009 | Yaung et al. |
| 7,547,872 B2 | 6/2009 | Niclass et al. |
| 7,613,504 B2 | 11/2009 | Rowe |
| 7,667,400 B1 | 2/2010 | Goushcha |
| 7,705,284 B2 | 4/2010 | Inoue et al. |
| 7,714,292 B2 | 5/2010 | Agarwal et al. |
| 7,774,047 B2 | 8/2010 | Yamashita et al. |
| 7,899,506 B2 | 3/2011 | Xu et al. |
| 8,026,471 B2 | 9/2011 | Itzler |
| 8,078,250 B2 | 12/2011 | Chen et al. |
| 8,082,015 B2 | 12/2011 | Yodh et al. |
| 8,115,170 B2 | 2/2012 | Stellari et al. |
| 8,168,934 B2 | 5/2012 | Niclass et al. |
| 8,633,431 B2 | 1/2014 | Kim |
| 8,637,875 B2 | 1/2014 | Finkelstein et al. |
| 8,754,378 B2 | 6/2014 | Prescher et al. |
| 8,817,257 B2 | 8/2014 | Herve |
| 8,986,207 B2 * | 3/2015 | Li .......................... A61B 5/72 600/301 |
| 9,012,860 B2 | 4/2015 | Nyman et al. |
| 9,041,136 B2 | 5/2015 | Chia |
| 9,058,081 B2 | 6/2015 | Baxter |
| 9,076,707 B2 | 7/2015 | Harmon |
| 9,101,279 B2 | 8/2015 | Ritchey et al. |
| 9,131,861 B2 | 9/2015 | Ince et al. |
| 9,160,949 B2 | 10/2015 | Zhang et al. |
| 9,176,241 B2 | 11/2015 | Frach |
| 9,178,100 B2 | 11/2015 | Webster et al. |
| 9,190,552 B2 | 11/2015 | Brunel et al. |
| 9,201,138 B2 | 12/2015 | Eisele et al. |
| 9,209,320 B1 | 12/2015 | Webster |
| 9,257,523 B2 | 2/2016 | Schneider et al. |
| 9,257,589 B2 | 2/2016 | Niclass et al. |
| 9,299,732 B2 | 3/2016 | Webster et al. |
| 9,299,873 B2 | 3/2016 | Mazzillo et al. |
| 9,312,401 B2 | 4/2016 | Webster |
| 9,316,735 B2 | 4/2016 | Baxter |
| 9,331,116 B2 | 5/2016 | Webster |
| 9,368,487 B1 | 6/2016 | Su et al. |
| 9,401,448 B2 | 7/2016 | Bienfang et al. |
| 9,407,796 B2 | 8/2016 | Dinten et al. |
| 9,419,635 B2 | 8/2016 | Kumar et al. |
| 9,431,439 B2 | 8/2016 | Soga et al. |
| 9,442,201 B2 | 9/2016 | Schmand et al. |
| 9,449,377 B2 | 9/2016 | Sarkar et al. |
| 9,450,007 B1 | 9/2016 | Motta et al. |
| 9,466,631 B2 | 10/2016 | Fallica et al. |
| 9,476,979 B2 | 10/2016 | Drader et al. |
| 9,478,579 B2 | 10/2016 | Dai et al. |
| 9,529,079 B1 | 12/2016 | Droz |
| 9,535,157 B2 | 1/2017 | Caley et al. |
| 9,574,936 B2 | 2/2017 | Heinonen |
| 9,625,580 B2 | 4/2017 | Kotelnikov et al. |
| 9,627,569 B2 | 4/2017 | Harmon |
| 9,639,063 B2 | 5/2017 | Dutton et al. |
| 9,640,704 B2 | 5/2017 | Frey et al. |
| 9,658,158 B2 | 5/2017 | Renna et al. |
| 9,659,980 B2 | 5/2017 | McGarvey et al. |
| 9,671,284 B1 | 6/2017 | Dandin |
| 9,685,576 B2 | 6/2017 | Webster |
| 9,702,758 B2 | 7/2017 | Nouri |
| 9,728,659 B2 | 8/2017 | Hirigoyen et al. |
| 9,741,879 B2 | 8/2017 | Frey et al. |
| 9,753,351 B2 | 9/2017 | Eldada |
| 9,767,246 B2 | 9/2017 | Dolinsky et al. |
| 9,768,211 B2 | 9/2017 | Harmon |
| 9,773,930 B2 | 9/2017 | Motta et al. |
| 9,804,092 B2 | 10/2017 | Zeng et al. |
| 9,812,438 B2 | 11/2017 | Schneider et al. |
| 9,831,283 B2 | 11/2017 | Shepard et al. |
| 9,851,302 B2 | 12/2017 | Mattioli Della Rocca et al. |
| 9,867,250 B1 | 1/2018 | Powers et al. |
| 9,869,753 B2 | 1/2018 | Eldada |
| 9,881,963 B1 | 1/2018 | Chen et al. |
| 9,882,003 B1 | 1/2018 | Aharoni |
| 9,886,095 B2 | 2/2018 | Pothier |
| 9,899,544 B1 | 2/2018 | Mazzillo et al. |
| 9,899,557 B2 | 2/2018 | Muscara' et al. |
| 9,939,316 B2 | 4/2018 | Scott et al. |
| 9,939,536 B2 | 4/2018 | O'Neill et al. |
| 9,946,344 B2 | 4/2018 | Ayaz et al. |
| D817,553 S | 5/2018 | Aaskov et al. |
| 10,016,137 B1 | 7/2018 | Yang et al. |
| D825,112 S | 8/2018 | Saez |
| 10,056,415 B2 | 8/2018 | Na et al. |
| 10,141,458 B2 | 11/2018 | Zhang et al. |
| 10,157,954 B2 | 12/2018 | Na et al. |
| 10,158,038 B1 | 12/2018 | Do Valle et al. |
| 10,219,700 B1 | 3/2019 | Yang et al. |
| 10,256,264 B2 | 4/2019 | Na et al. |
| 10,340,408 B1 | 7/2019 | Katnani |
| 10,424,683 B1 | 9/2019 | Do Valle |
| 10,515,993 B2 | 12/2019 | Field et al. |
| 10,558,171 B2 | 2/2020 | Kondo |
| 10,809,796 B2 | 10/2020 | Armstrong-Muntner |
| 2005/0061986 A1 | 3/2005 | Kardynal et al. |
| 2007/0038116 A1* | 2/2007 | Yamanaka ......... A61B 5/14553 600/476 |
| 2009/0012402 A1 | 1/2009 | Mintz |
| 2009/0163775 A1* | 6/2009 | Barrett ................ A61B 5/0059 600/301 |
| 2011/0208675 A1 | 8/2011 | Shoureshi et al. |
| 2012/0029304 A1 | 2/2012 | Medina et al. |
| 2013/0030267 A1* | 1/2013 | Lisogurski ......... A61B 5/14553 600/324 |
| 2013/0032713 A1 | 2/2013 | Barbi et al. |
| 2013/0221221 A1 | 8/2013 | Bouzid et al. |
| 2013/0342835 A1 | 12/2013 | Blacksberg |
| 2014/0027607 A1 | 1/2014 | Mordarski et al. |
| 2014/0191115 A1 | 7/2014 | Webster et al. |
| 2014/0211194 A1 | 7/2014 | Pacala et al. |
| 2014/0275891 A1 | 9/2014 | Muehlemann et al. |
| 2014/0291481 A1 | 10/2014 | Zhang et al. |
| 2015/0041625 A1 | 2/2015 | Dutton |
| 2015/0041627 A1 | 2/2015 | Webster |
| 2015/0054111 A1 | 2/2015 | Niclass et al. |
| 2015/0077279 A1 | 3/2015 | Song |
| 2015/0150505 A1 | 6/2015 | Kaskoun et al. |
| 2015/0192677 A1 | 7/2015 | Yu et al. |
| 2015/0200222 A1 | 7/2015 | Webster |

(56) References Cited

U.S. PATENT DOCUMENTS

| | | | |
|---|---|---|---|
| 2015/0293224 A1 | 10/2015 | Eldada et al. | |
| 2015/0327777 A1 | 11/2015 | Kostic et al. | |
| 2015/0333095 A1 | 11/2015 | Fallica et al. | |
| 2015/0364635 A1 | 12/2015 | Bodlovic et al. | |
| 2016/0049765 A1 | 2/2016 | Eldada | |
| 2016/0099371 A1 | 4/2016 | Webster | |
| 2016/0119983 A1 | 4/2016 | Moore | |
| 2016/0150963 A1 | 6/2016 | Roukes et al. | |
| 2016/0161600 A1 | 6/2016 | Eldada et al. | |
| 2016/0181302 A1 | 6/2016 | McGarvey et al. | |
| 2016/0218236 A1 | 7/2016 | Dhulla et al. | |
| 2016/0278715 A1 | 9/2016 | Yu et al. | |
| 2016/0287107 A1 | 10/2016 | Szabados | |
| 2016/0341656 A1 | 11/2016 | Liu et al. | |
| 2016/0356718 A1 | 12/2016 | Yoon et al. | |
| 2016/0357260 A1 | 12/2016 | Raynor et al. | |
| 2017/0030769 A1 | 2/2017 | Clemens et al. | |
| 2017/0047372 A1 | 2/2017 | McGarvey et al. | |
| 2017/0052065 A1 | 2/2017 | Sharma et al. | |
| 2017/0118423 A1 | 4/2017 | Zhou et al. | |
| 2017/0131143 A1 | 5/2017 | Andreou et al. | |
| 2017/0139041 A1 | 5/2017 | Drader et al. | |
| 2017/0141100 A1 | 5/2017 | Tseng et al. | |
| 2017/0176579 A1 | 6/2017 | Niclass et al. | |
| 2017/0176596 A1 | 6/2017 | Shpunt et al. | |
| 2017/0179173 A1 | 6/2017 | Mandai et al. | |
| 2017/0186798 A1 | 6/2017 | Yang et al. | |
| 2017/0202518 A1 | 7/2017 | Furman et al. | |
| 2017/0265822 A1 | 9/2017 | Du | |
| 2017/0276545 A1 | 9/2017 | Henriksson | |
| 2017/0281086 A1* | 10/2017 | Donaldson | A61B 5/14532 |
| 2017/0299700 A1 | 10/2017 | Pacala et al. | |
| 2017/0303789 A1 | 10/2017 | Tichauer et al. | |
| 2017/0314989 A1 | 11/2017 | Mazzillo et al. | |
| 2017/0363467 A1 | 12/2017 | Clemens et al. | |
| 2018/0003821 A1 | 1/2018 | Imai | |
| 2018/0014741 A1 | 1/2018 | Chou | |
| 2018/0019268 A1 | 1/2018 | Zhang et al. | |
| 2018/0026147 A1 | 1/2018 | Zhang et al. | |
| 2018/0027196 A1 | 1/2018 | Yang et al. | |
| 2018/0033895 A1 | 2/2018 | Mazzillo et al. | |
| 2018/0039053 A1 | 2/2018 | Kremer et al. | |
| 2018/0045816 A1 | 2/2018 | Jarosinski et al. | |
| 2018/0062345 A1 | 3/2018 | Bills et al. | |
| 2018/0069043 A1 | 3/2018 | Pan et al. | |
| 2018/0081061 A1 | 3/2018 | Mandai et al. | |
| 2018/0089848 A1 | 3/2018 | Yang et al. | |
| 2018/0090526 A1 | 3/2018 | Mandai et al. | |
| 2018/0090536 A1 | 3/2018 | Mandai et al. | |
| 2018/0102442 A1 | 4/2018 | Wang et al. | |
| 2018/0103528 A1 | 4/2018 | Moore | |
| 2018/0167606 A1 | 6/2018 | Cazaux et al. | |
| 2018/0175230 A1 | 6/2018 | Droz et al. | |
| 2018/0217261 A1 | 8/2018 | Wang | |
| 2018/0366342 A1 | 12/2018 | Inoue et al. | |
| 2019/0006399 A1 | 1/2019 | Otake et al. | |
| 2019/0088697 A1 | 3/2019 | Furukawa et al. | |
| 2019/0113385 A1 | 4/2019 | Fukuchi | |
| 2019/0175068 A1* | 6/2019 | Everdell | A61B 5/14552 |
| 2019/0355773 A1 | 11/2019 | Field et al. | |
| 2019/0378869 A1 | 12/2019 | Field et al. | |
| 2020/0196932 A1 | 6/2020 | Johnson | |
| 2020/0315510 A1 | 10/2020 | Johnson | |
| 2020/0337624 A1 | 10/2020 | Johnson | |
| 2020/0390358 A1 | 12/2020 | Johnson | |

FOREIGN PATENT DOCUMENTS

| | | |
|---|---|---|
| WO | 8804034 | 6/1988 |
| WO | 2008144831 | 12/2008 |
| WO | 2012135068 | 10/2012 |
| WO | 2013034770 | 3/2013 |
| WO | 2013066959 | 5/2013 |
| WO | 2015052523 | 4/2015 |
| WO | 2016166002 | 10/2016 |
| WO | 2017004663 | 1/2017 |
| WO | 2017130682 | 8/2017 |
| WO | 2017150146 | 9/2017 |
| WO | 2017203936 | 11/2017 |
| WO | 2018007829 | 1/2018 |
| WO | 2018033751 | 2/2018 |
| WO | 2018122560 | 7/2018 |

OTHER PUBLICATIONS

International Search Report and Written Opinion received in International Application No. PCT/2020/028820, dated Aug. 26, 2020.
International Search Report and Written Opinion received in International Application No. PCT/US20/34062, dated Aug. 26, 2020.
International Search Report and Written Opinion received in International Application No. PCT/US2018/058580, dated Feb. 12, 2019.
International Search Report and Written Opinion received in International Application No. PCT/US2018/062777, dated Feb. 13, 2019.
International Search Report and Written Opinion received in International Application No. PCT/US2019/019317, dated May 28, 2019.
Non-Final Office Action received in U.S. Appl. No. 16/177,351, dated Apr. 1, 2019.
Non-Final Office Action received in U.S. Appl. No. 16/283,730, dated May 16, 2019.
Non-Final Office Action received in U.S. Appl. No. 16/370,991, dated Feb. 10, 2020.
Non-Final Office Action received in U.S. Appl. No. 16/537,360, dated Feb. 25, 2020.
Non-Final Office Action received in U.S. Appl. No. 16/544,850, dated Jun. 25, 2020.
Non-Final Office Action received in U.S. Appl. No. 16/856,524, dated Dec. 1, 2020.
Partial Search Report received in International Application No. PCT/2020/028820, dated Jul. 1, 2020.
Partial Search Report received in International Application No. PCT/2020/027537, dated Jul. 17, 2020.
Alayed, et al.,"Characterization of a Time-Resolved Diffuse Optical Spectroscopy Prototype Using Low-Cost, Compact Single Photon Avalanche Detectors for Tissue Optics Applications," Sensors 2018, 18, 3680; doi:10.3390/s18113680.
Bellis, Stephen et al.,"Photon counting imaging: the DigitalAPD," Society of Photo-Optical Instrumentation Engineers (SPIE) Conference Series, Feb. 2006, vol. 6068, pp. 111-120.
Blutman, et al.,"A 0.1 pJ Freeze Vernler Time-to-Digital Converter in 65nm CMOS," 2014 International Symposium on Circuits and Systems (ISCAS), Melbourne, Australia.
Cambie, Dario et al.,"Every photon counts: understanding and optimizing photon paths in luminescent solar concentrator-based photomicroreactors (LSC-PMs)," React. Chem. Eng., 2017, 2, 561-566.
Contini, et al.,"Photon migration through a turbid slab described by a model based on diffusion approximation. I. Theory," Appl. Opt. 36(19), 4587 (1997).
Dalla Mora, et al.,"Fast-Gated Single-Photon Avalanche Diode for Wide Dynamic Range Near Infrared Spectroscopy," IEEE Journal of Selected Topics in Quantum Electronics, vol. 16, No. 4, Jul./Aug. 2010 ,2010 ,1023-1030.
Dalla Mora, et al.,"Memory effect in silicon time-gated single-photon avalanche diodes," http://dx.dol.org/10.1063/1.4915332, Journal of Applied Physics 117, 114501, 2015 ,2015 ,1-7.
De Heyn, et al.,"A fast start-up 3GHz-10GHz digitally controlled oscillator for UWB impulse radio in 90nm CMOS," 2007 European Solid-State Circuits Conference—(ESSCIRC), Munich, Germany, pp. 484-487.
De Sieno, et al.,"Probe-hosted large area silicon photomultiplier and high-throughput timing electronics for enhanced performance time-domain functional near-infrared spectroscopy," Biomed. Opt. Express 11(11), 6389 (2020).
Dutton, et al.,"A Time-Correlated Single-Photon-Counting Sensor with 14GS/s Histogramming Time-to-Digital Converter," 2015 IEEE

(56) References Cited

OTHER PUBLICATIONS

International Solid-State Circuits Conference ISSCC 2015 / Session 11 / Sensors and Imagers for Life Sciences / 11.5.

Fishburn, et al.,"Temporal Derivative Distribution Repair (TDDR): A motion correction method for fNIRS," Neuroimage. Jan. 1, 2019; 184: 171-179. doi:10.1016/j.neuroimage.2018.09.025.

Fisher, et al.,"A Reconfigurable Single-Photon-Counting Integrating Receiver for Optical Communications," IEEE Journal of Solid-State Circuits, vol. 48, No. 7, Jul. 2013, https://www.researchgate.net/publication/260626902.

Gallivanoni, et al.,"Progress in Quenching Circuits for Single Photon Avalanche Diodes," IEEE Transactions on Nuclear Science, vol. 57, No. 6, Dec. 2010.

Gnecchi, et al.,"A 1×16 SiPM Array for Automotive 3D Imaging LIDAR Systems."

Harmon, Eric S. et al.,"Compound Semiconductor SPAD Arrays, LightSpin Technologles," http://www.lightspintech.com/publications.html.

Henderson, et al.,"A 192×128 Time Correlated SPAD Image Sensor in 40-nm CMOS Technology," IEEE Journal of Solid-State Circuits, IEEE Journal of Solid-State Circuits, 2019.

Henderson, et al.,"A 256×256 40nm/90nm CMOS 3D-Stacked 120dB Dynamic-Range Reconfigurable Time-Resolved SPAD Imager," 2019 IEEE International Solid-State Circuits Conference—(ISSCC), San Francisco, CA, USA, 2019, pp. 106-108. doi: 10.1109/ISSCC.2019.8662355.

Huppert, et al.,"HomER: a review of time-series analysis methods for near-infrared spectroscopy of the brain," Appl. Opt. 48(10), D280 (2009).

Kienle, et al.,"Improved solutions of the steady-state and the time-resolved diffusion equations for reflectance from a semi-infinite turbid medium," J. Opt. Soc. Am, A 14(1), 246 (1997).

Konugolu, et al.,"Broadband (600-1350 nm) Time-Resolved Diffuse Optical Spectrometer for Clinical Use," IEEE Journal of Selected Topics in Quantum Electronics, vol. 22, No. 3, May/Jun. 2016.

Lacerenza, et al.,"Wearable and wireless time-domain near-infrared spectroscopy system for brain and muscle hemodynamic monitoring," Biomed. Opt. Express 11(10), 5934 (2020).

Lange, et al.,"Clinical Brain Monitoring with Time Domain NIRS: A Review and Future Perspectives," Applied Sciences 9(8), 1612 (2019).

Lange, et al.,"Maestros: A Multiwavelength Time-Domain NIRS System to Monitor Changes in Oxygenation and Oxidation State of Cytochrome-C-Oxidase," IEEE J. Select. Topics Quantum Electron. 25(1), 1-12 (2019).

Lee, et al.,"High-Performance Back-Illuminated Three-Dimensional Stacked Single-Photon Avalanche Diode Implemented in 45-nm CMOS Technology," IEEE Journal of Selected Topics in Quantum Electronics 6, 1-9 (2018).

Mandai, et al.,"A 4×4×416 digital SIPM array with 192 TDCs for multiple high-resolution timestamp acquisition," 2013 JINST 8 PO5024.

Martelli, et al.,"Optimal estimation reconstruction of the optical properties of a two-layered tissue phantom from time-resolved single-distance measurements," Journal of Biomedical Optics 20(11), 115001 (Nov. 2015).

Maruyama, et al.,"A 1024×8, 700-ps Time-Gated SPAD Line Sensor for Planetary Surface Exploration With Laser Raman Spectroscopy and LIBS," IEEE Journal of Solid-State Circuits, vol. 49, No. 1, Jan. 2014 ,2014 ,179-189.

Mita, et al.,"High-Speed and Compact Quenching Circuit for Single-Photon Avalanche Diodes," IEEE Transactions on Instrumentation and Measurement, vol. 57, No. 3, Mar. 2008, pp. 543-547.

Mora, et al.,"Fast silicon photomultiplier improves signal harvesting and reduces complexity in time-domain diffuse optics," Opt. Express 23(11), 13937 (2015).

Mora, Alberto D. et al.,"Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.

Parmesan, et al.,"A 256×256 SPAD array with in-pixel Time to Amplitude Conversion for Fluorescence Lifetime Imaging Microscopy," 2015.

Pifferi, et al.,"Performance assessment of photon migration instruments: the MEDPHOT protocol," Applied Optics, 44(11), 2104-2114.

Prahl, et al.,"Optical Absorption of Hemoglobin," http://omic.ogi.edu/spectra/hemoglobin/index.html.

Puszka et al.,"Time-resolved diffuse optical tomography using fast-gated single-photon avalanche diodes," Biomedical optics express, 2013, vol. 4, No. 8, pp. 1351-1365 (Year: 2013).

Re, et al.,"Multi-channel medical device for time domain functional near infrared spectroscopy based on wavelength space multiplexing," Biomed. Opt. Express 4(10), 2231 (2013).

Renna, et al.,"Eight-Wavelength, Dual Detection Channel Instrument for Near-Infrared Time-Resolved Diffuse Optical Spectroscopy," IEEE J. Select, Topics Quantum Electron. 25(1), 1-11 (2019).

Richardson, et al.,"A 32×32 50ps resolution 10 bit time to digital converter array in 130nm CMOS for time correlated imaging," CICC 2009 Proceedings of the IEEE 2009 Custom Integrated Circuits Conference. IEEE Society, San Jose, U.S.A., pp. 77-80, CICC 2009, San Jose, U.S.A., Sep. 13, 2009. https://doi.org/dol:10.1109/CICC.2009.5280890.

Takai, et al.,"Single-Photon Avalanche Diode with Enhanced NIR-Sensitivity for Automotive LIDAR Systems," Sensors, 2016, 16(4): 459, pp. 1-9 (Year: 2016).

Torricelli, et al.,"Time domain functional NIRS imaging for human brain mapping," Neuroimage 85, 28-50 (2014).

Wabnitz, et al.,"Depth-selective data analysis for time-domain fNIRS: moments vs. time windows," Biomed. Opt. Express 11(8), 4224 (2020).

Wabnitz, et al.,"Performance assessment of time-domain optical brain imagers, part 1: basic instrumental performance protocol," Journal of Biomedical Optics 19(8), 086010 (Aug. 2014).

Wabnitz, et al.,"Performance assessment of time-domain optical brain imagers, part 2: nEUROPt protocol," Journal of Biomedical Optics 19(8), 086012 (Aug. 2014).

Wojtkiewicz, et al.,"Self-calibrating time-resolved near infrared spectroscopy," Biomed. Opt. Express 10(5), 2657 (2019).

Zhang, et al.,"A CMOS SPAD Imager with Collision Detection and 128 Dynamically Reallocating TDCs for Single-Photon Counting and 3D Time-of-Flight Imaging," Sensors (Basel, Switzerland), 18(11), 4016. doi:10.3390/s18114016.

Zucchelli, et al.,"Method for the discrimination of superficial and deep absorption variations by time domain fNiRS," 2013 OSA Dec. 1, 2013 | vol. 4, No. 12 | DOI:10.1364/BOE.4.002893 | Biomedical Optics Express 2893.

\* cited by examiner

WEARABLE MODULE ASSEMBLIES FOR AN OPTICAL MEASUREMENT SYSTEM

RELATED APPLICATIONS

The present application claims priority under 35 U.S.C. § 119(e) to U.S. Provisional Patent Application No. 63/081,754, filed on Sep. 22, 2020, and to U.S. Provisional Patent Application No. 62/992,550, filed on Mar. 20, 2020, and to U.S. Provisional Patent Application No. 62/979,866, filed on Feb. 21, 2020. These applications are incorporated herein by reference in their respective entireties.

BACKGROUND INFORMATION

Detecting neural activity in the brain (or any other turbid medium) is useful for medical diagnostics, imaging, neuroengineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
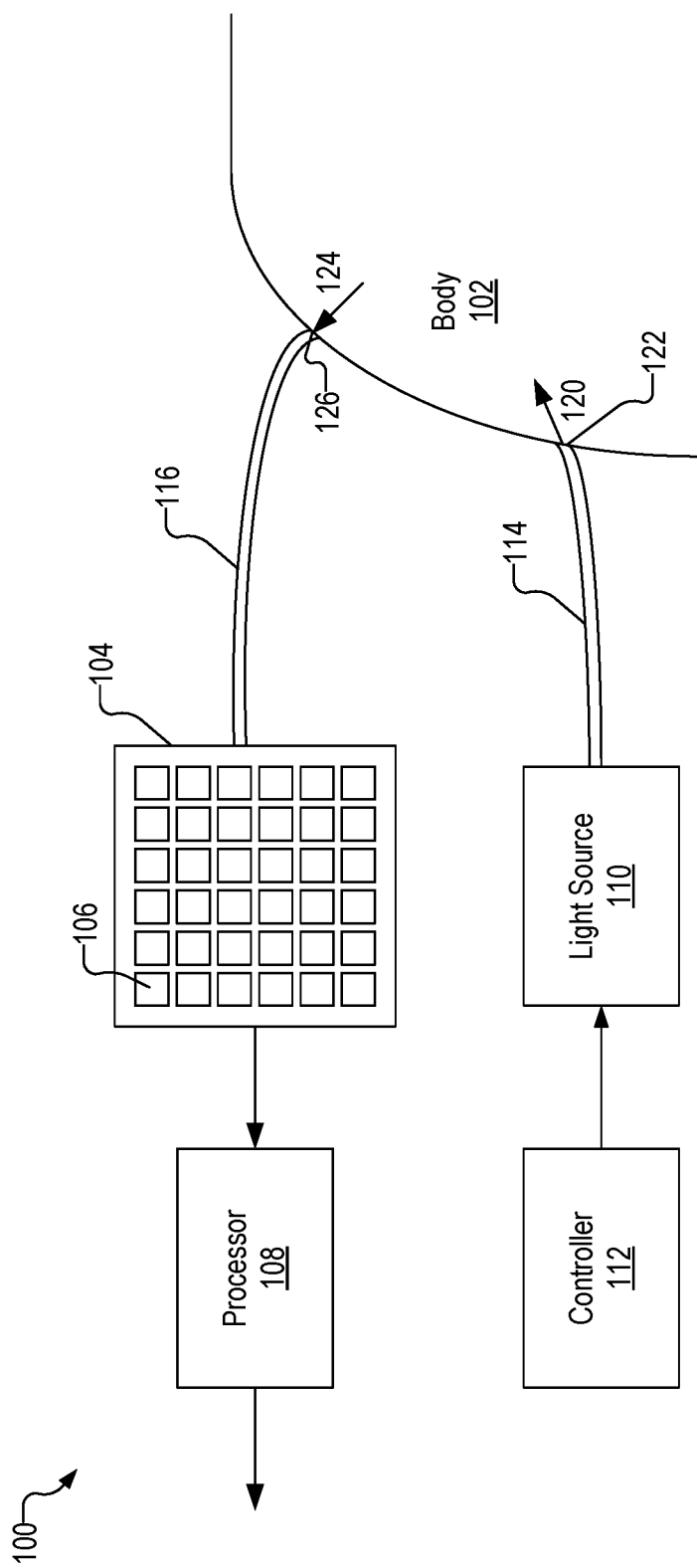
FIG. 1 illustrates an exemplary optical measurement system.

Optical measurement systems and wearable assemblies for use in the optical measurement systems are described herein. An exemplary optical measurement system includes a wearable module assembly. The wearable module assembly is configured to be worn on a body of a user and includes a plurality of wearable modules and a connecting assembly. Each wearable module includes a light source configured to emit a light pulse toward a target within the body of the user and a plurality of detectors configured to receive photons included in the light pulse after the photons are scattered by the target. The connecting assembly physically connects the plurality of wearable modules. The connecting assembly may flexibly connect the plurality of wearable modules such that the wearable module assembly is conformable to a three-dimensional (3D) surface of the body of the user when the wearable module assembly is worn on the body of the user. In some examples, the connecting assembly may maintain a uniform spacing between adjacent wearable modules included in the plurality of wearable modules. The plurality of detectors of a wearable module may be separated from the light source of the wearable module by a fixed source-detector distance, and the fixed source-detector distance may be substantially the same for each wearable module included the plurality of wearable modules.

The optical measurement systems and wearable assemblies described herein provide various benefits. For example, the wearable module assemblies described herein can conform to a 3D surface of a user's body (such as the user's head), maintain tight contact of the detectors with the user's body to prevent detection of ambient light, and maintain uniform and fixed spacing between light sources and detectors. The wearable module assemblies may also accommodate a large variety of head sizes, from a young child's head size to an adult head size, and may accommodate a variety of head shapes and underlying cortical morphologies through the conformability and scalability of the wearable module assemblies. Additionally, the uniform and fixed light source and detector spacing of the conformable wearable module assemblies allows the optical measurement systems to process the detected signals to infer spatial (e.g., depth localization, inverse modeling) information about the detected signals. Moreover, the uniform and fixed light source and detector spacing of the conformable wearable module assemblies provides consistent spatial (lateral and depth) resolution across the imaged area. The conformable wearable module assemblies described herein also help maintain the light sources and detectors in physical contact with the 3D surface, thereby minimizing or even eliminating the detection of ambient light that would otherwise contaminate the detected signals. These and other advantages and benefits of the present systems and assemblies are described more fully herein and/or will be made apparent in the description herein.

FIG. 1 shows an exemplary optical measurement system 100 configured to perform an optical measurement operation with respect to a body 102. Optical measurement system 100 may, in some examples, be portable and/or wearable by a user.

In some examples, optical measurement operations performed by optical measurement system 100 are associated with a time domain-based optical measurement technique. Example time domain-based optical measurement techniques include, but are not limited to, TCSPC, time domain near infrared spectroscopy (TD-NIRS), time domain diffusive correlation spectroscopy (TD-DCS), and time domain digital optical tomography (TD-DOT).

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light guides, as described more fully herein). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as 2" photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diode (sLEDs), vertical-cavity surface-emitting lasers (VCSELs), titanium sapphire lasers, a micro light emitting diodes (mLEDs), and/or any other suitable laser or light source configured to emit light in one or more discrete wavelengths or narrow wavelength bands. In some examples, the light emitted by light source 110 is high coherence light (e.g., light that has a coherence length of at least 5 centimeters) at a predetermined center wavelength. In some examples, the light emitted by light source 110 is emitted as a plurality of alternating light pulses of different wavelengths.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 travels via an optical conduit 114 (e.g., a light pipe, a light guide, a waveguide, a single-mode optical fiber, and/or or a multi-mode optical fiber) to body 102 of a subject. Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., tissue, blood flow, etc.) in body 102. Example embodiments of accumulated outputs are described herein.

Figure 2:
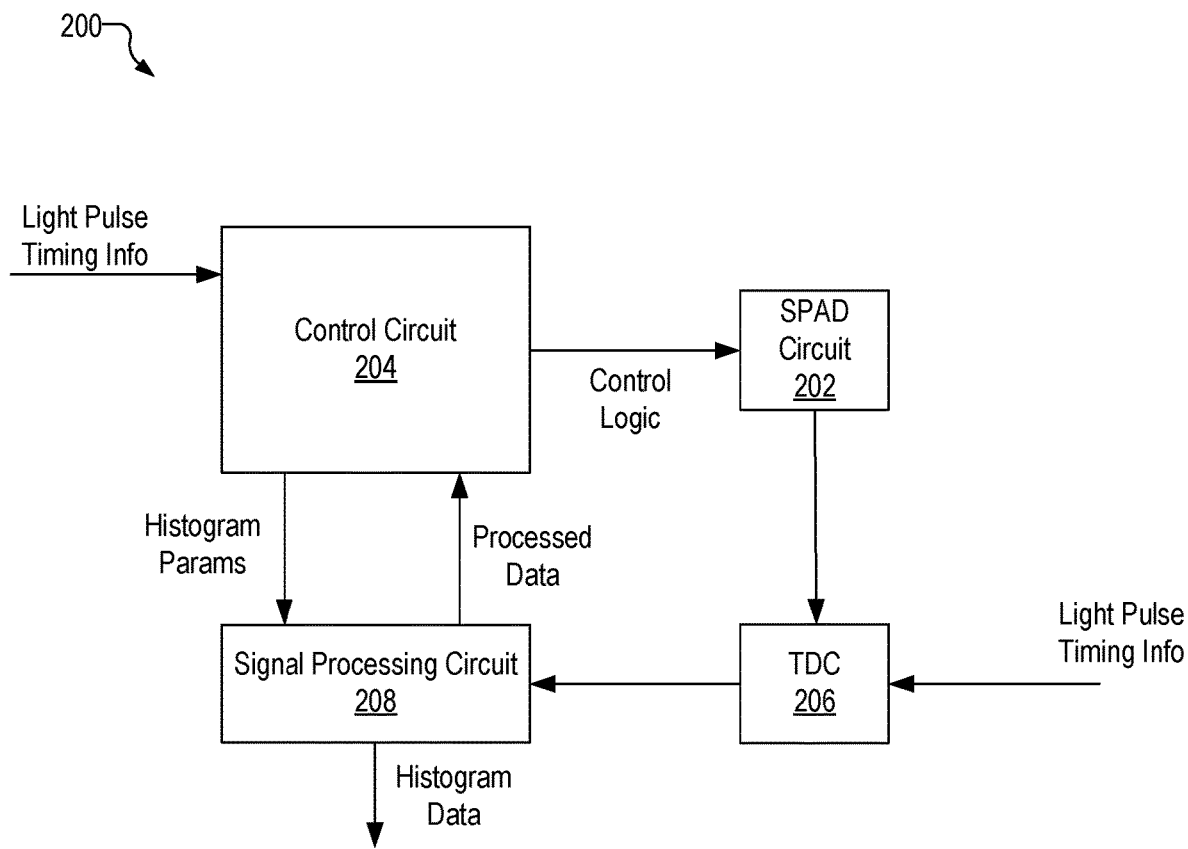
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for one or more SPAD circuits 202 and/or TDCs 206.

Figure 3:
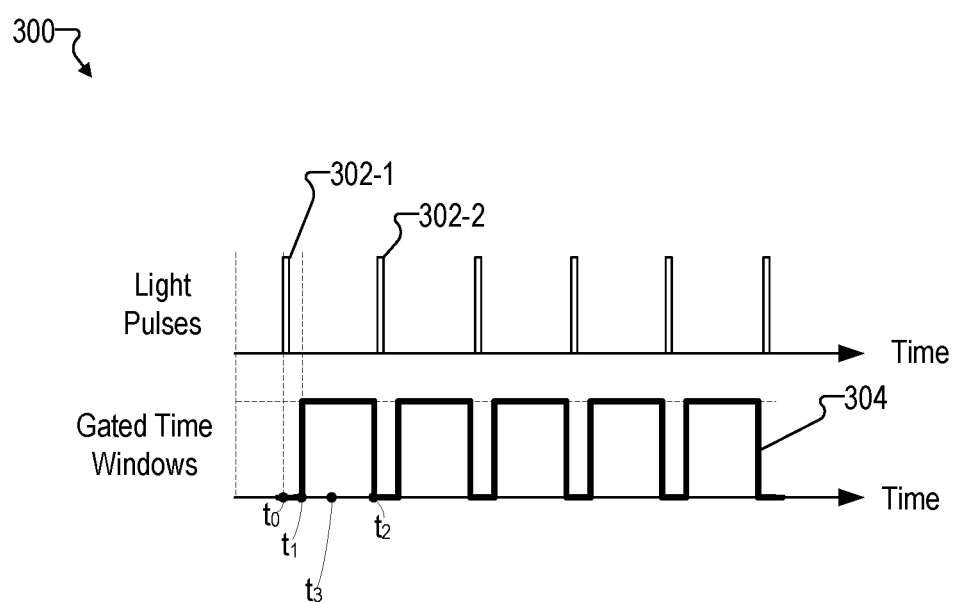
FIG. 3 illustrates an exemplary timing diagram for performing an optical measurement operation using an optical measurement system.

FIG. 3 illustrates an exemplary timing diagram 300 for performing an optical measurement operation using optical measurement system 100. The optical measurement operation may be performed in accordance with a time domain-based technique, such as TD-NIRS. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and at least a portion of the scattered light may be detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

Timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. As shown, light pulse 302-1 is applied at a time $t_0$. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

Figure 4:
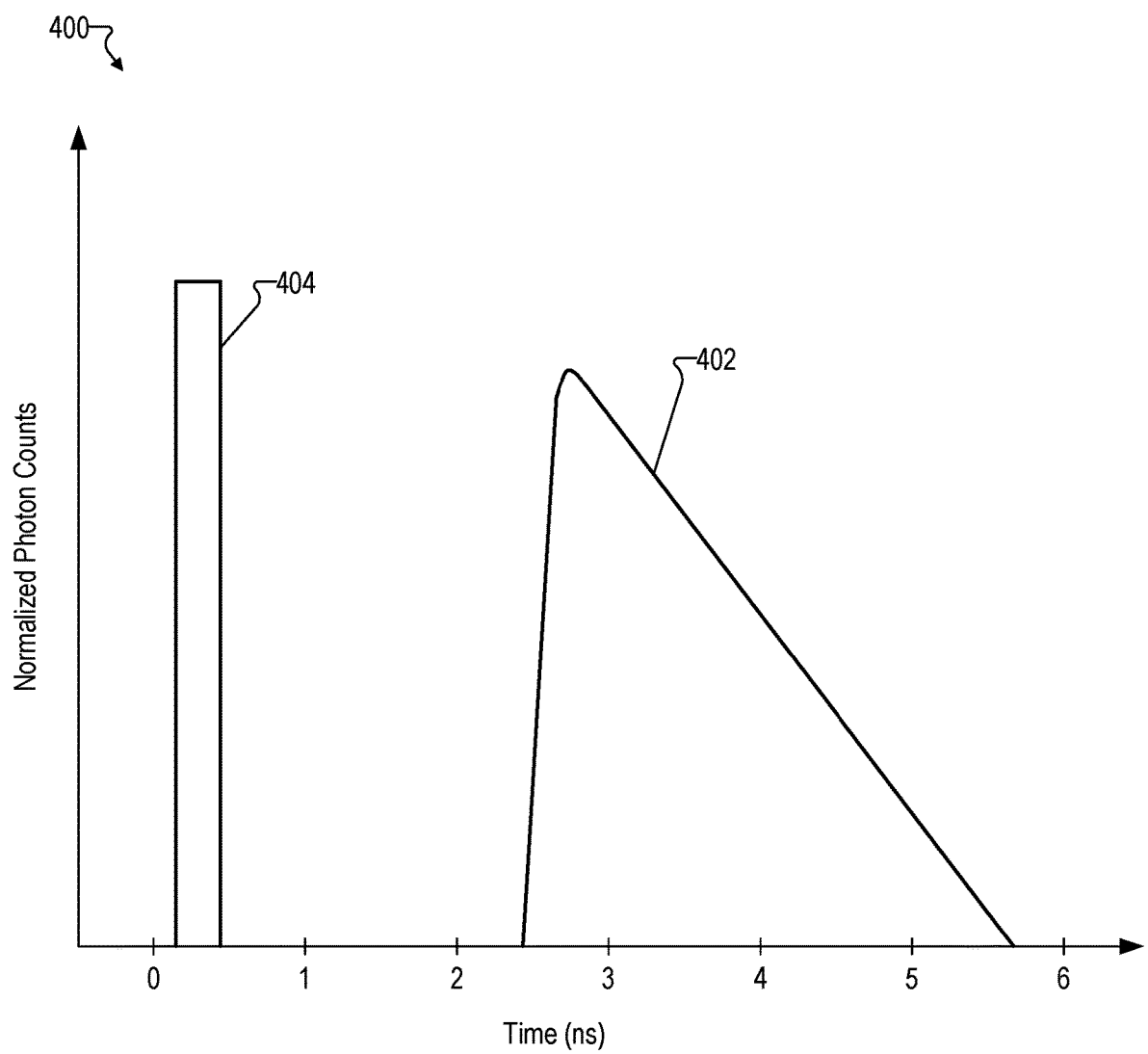
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer biological (e.g., neural) activity.

Optical measurement system 100 may be implemented by or included in any suitable device(s). For example, optical measurement system 100 may be included in a non-wearable device (e.g., a medical device and/or consumer device that is placed near the head or other body part of a user to perform one or more diagnostic, imaging, and/or consumer-related operations). Optical measurement system 100 may alternatively be included, in whole or in part, in a sub-assembly enclosure of a wearable invasive device (e.g., an implantable medical device for brain recording and imaging).

Alternatively, optical measurement system 100 may be included, in whole or in part, in a non-invasive wearable device that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
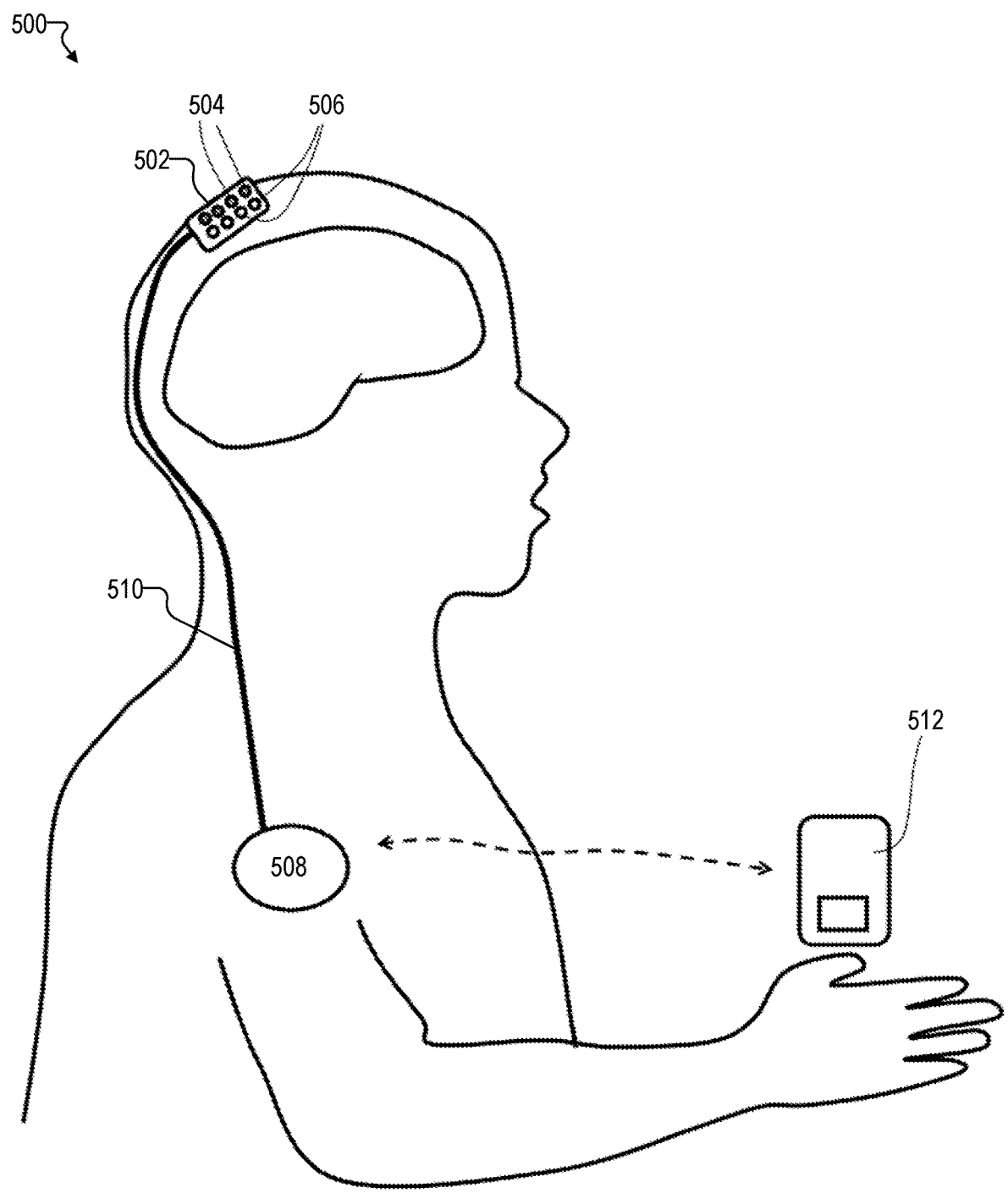
FIG. 5 illustrates an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to and/or worn on a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described below in more detail and in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and/or for transforming photodetector measurements into an intensity value that represents an optical property of a target within the brain. Brain interface system 500 allows optical detection of deep anatomical locations beyond skin and bone (e.g., skull) by extracting data from photons originating from light sources 506 and emitted to a target location within the user's brain, in contrast to conventional imaging systems and methods (e.g., optical coherence tomography (OCT), continuous wave near infrared spectroscopy (CW-NIRS)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506. In some examples, processor 508 is implemented by or similar to processor 108 and/or controller 112.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). In some examples, remote processor 512 is implemented by or similar to processor 108 and/or controller 112.

Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and/or in another wearable or non-wearable device and coupled to head mountable component 502 through an optical connection.

In some alternative embodiments, head mountable component 502 does not include individual detectors 504. Instead, one or more detectors configured to detect the scattered light from the target may be included elsewhere in brain interface system 500. For example, a detector may be included in processor 508 and/or in another wearable or non-wearable device and coupled to head mountable component 502 through an optical connection.

Figure 6:
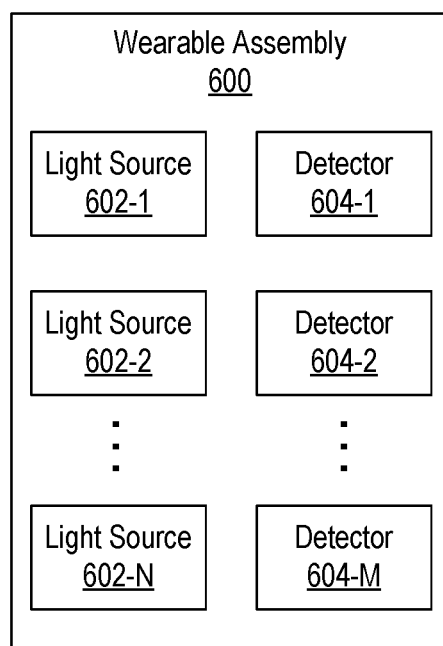
FIG. 6 shows a functional diagram of an exemplary wearable assembly that may implement, or be included in an implementation of, an optical measurement system.

FIG. 6 shows a functional diagram of an exemplary wearable assembly 600 that may implement, or be included in an implementation of, optical measurement system 100. Wearable assembly 600 includes N light sources 602 (e.g., light sources 602-1 through 602-N) and M detectors 604 (e.g., detectors 604-1 through 604-M). Wearable assembly 600 may include any of the other components of optical measurement system 100 as may serve a particular implementation. N and M may each be any suitable value (i.e., there may be any number of light sources 602 and any number of detectors 604 included in wearable assembly 600 as may serve a particular implementation).

Light sources 602 are each configured to emit light (e.g., a sequence of light pulses) and may be implemented by any of the light sources described herein. Detectors 604 may each be configured to detect arrival times for photons of the light emitted by one or more light sources 602 after the light is scattered by the target. For example, a detector 604 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector). Detectors 604 may be implemented by any of the detectors described herein.

Wearable assembly 600 may be implemented by any of the wearable devices, wearable module assemblies, and/or wearable units described herein. For example, wearable assembly 600 may be implemented by a wearable device (e.g., headgear) configured to be worn on a user's head. Wearable assembly 600 may additionally or alternatively be implemented by a wearable device configured to be worn on any other part of a user's body.

Wearable assembly 600 may be modular in that one or more components of wearable assembly 600 may be removed, changed out, or otherwise modified as may serve a particular implementation. Additionally or alternatively, wearable assembly 600 may be modular such that one or more components of wearable assembly 600 may be housed in a separate housing (e.g., module) and/or may be movable relative to other components. Exemplary modular assemblies and systems are described in more detail in U.S. Provisional Patent Application No. 63/081,754, filed Sep. 22, 2020, U.S. Provisional Patent Application No. 63/038, 459, filed Jun. 12, 2020, U.S. Provisional Patent Application No. 63/038,468, filed Jun. 12, 2020, U.S. Provisional Patent Application No. 63/038,481, filed Jun. 12, 2020, and U.S. Provisional Patent Application No. 63/064,688, filed Aug. 12, 2020, which applications are incorporated herein by reference in their respective entireties.

Figure 7:
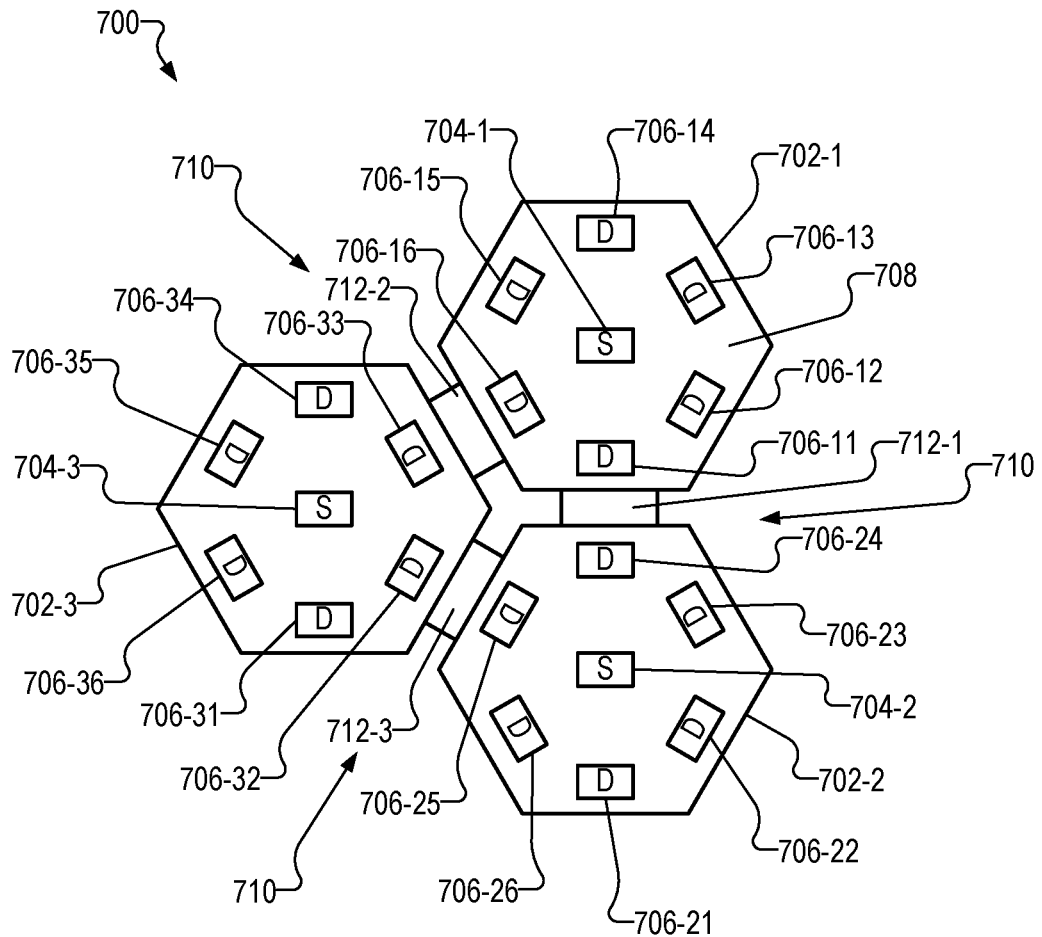
FIG. 7 illustrates an exemplary implementation in which the wearable assembly of FIG. 6 is implemented by a wearable module assembly.

FIG. 7 illustrates an exemplary implementation of wearable assembly 600. FIG. 7 is illustrative of one of many different implementations of wearable assembly 600 that may be realized in accordance with the principles described herein. As shown in FIG. 7, wearable assembly 600 is implemented by a wearable module assembly 700. Wearable module assembly 700 includes a plurality of wearable modules 702 (e.g., modules 702-1 through 702-3). Module 702-1 can represent or include a first module housing, module 702-2 can represent or include a separate second module housing, module 703-3 can represent or include a separate third module housing, and so forth. While three modules 702 are shown to be included in optical measurement system 700, in alternative configurations, any number of modules 702 (e.g., a single module up to sixteen or more modules) may be included in wearable module assembly 700.

Each module 702 includes a light source 704 (e.g., light source 704-1 of module 702-1, light source 704-2 of module 702-2, and light source 704-3 of module 702-3) and a plurality of detectors 706 (e.g., detectors 706-11 through 706-16 of module 702-1, detectors 706-21 through 706-26 of module 702-2, and detectors 706-31 through 706-36 of module 702-3). In the particular implementation shown in FIG. 7, each module 702 includes a single light source 704 (labeled "S") and six detectors 706 (each labeled "D"). However, each module 702 may have any other number and arrangement of light sources 704 and detectors 706 as may serve a particular implementation. Any one or more components of a module 702 (e.g., a light source 704, detectors 706, and/or any other components) may be housed, in whole or in part, within a module housing.

Each light source 704 may be implemented by any light source described herein and may be configured to emit a light pulse directed at a target (e.g., the brain). For example, light source 704-1 may emit a first light pulse toward the target and light source 704-2 may emit a second light pulse toward the target. In some examples, each light source 704 housed within module 702 includes one or more light-generating components (e.g., laser diodes). Each light source 704 may additionally include any suitable optical components (e.g., an optical conduit) configured to guide and direct emitted light toward the target. In some examples, a portion of each light source 704 (e.g., an optical conduit) protrudes from a front surface 708 of the module 702 (e.g., a surface of module 702 facing, or substantially parallel to a surface of, the body of the user when wearable module assembly 700 is worn by the user) to facilitate contact of light source 704 with the body of the user and/or to penetrate through the user's hair.

Each light source 704 may be located at a center region of front surface 708. In alternative implementations, a light source 704 of a module 702 may be located at any other location on the module. In alternative configurations (not shown) of a module 702, one or more components of the light source 704 (e.g., laser diodes) may be located remotely in/on another device separate from module 702, and the generated light may be conveyed to module 702 by another optical conduit (e.g., optical fibers, etc.).

Each detector 706 may be implemented by any detector described herein and may include a plurality of photodetectors (e.g., SPADs) as well as other circuitry (e.g., TDCs, RF antennas, inductive coupling coils) housed within module 702. Each detector 706 may be configured to detect arrival times for photons of the light emitted by one or more light sources after the photons are scattered by the target. For example, detector 706-11 may detect a first set of photons included in the first light pulse after the first set of photons are scattered by the target, and detector 706-21 may detect a second set of photons included in the second light pulse after the second set of photons are scattered by the target. In some examples, each detector 706 housed within module 702 may also include any suitable optical components (e.g., an optical conduit) configured to receive and guide photons scattered by the target toward the plurality of photodetectors included in the detector 706. In some examples, a portion of each detector 706 (e.g., an optical conduit) protrudes from front surface 708 to facilitate contact with the body of the user and/or to penetrate through the user's hair.

In alternative configurations (not shown) of a module 702, one or more components of a detector 706 (e.g., a photodetector) may be located remotely in/on another device separate from the module 702, and the scattered photons received by detector 706 are conveyed from the module 702 by another optical conduit (e.g., optical fibers, etc.) to the remote component.

As shown in FIG. 7, the detectors 706 of a module 702 may be distributed around light source 704 of the same module 702. In this configuration, detectors 706 may be configured to detect photon arrival times for photons included in light pulses emitted by the light source 704 and scattered by the target. In some examples, the detectors 706 of a module 702 may all be equidistant from the light source 704 of the same module. That is, the detectors 706 of a module 702 are separated from the light source 704 of the module 702 by the same source-detector distance. As used herein, the source-detector distance refers to the linear distance between the point where a light pulse emitted by a light source 704 exits module 702 (i.e., a distal end (light-emitting) surface of a light-emitting optical conduit of light source 704) and the point where photons included in the light pulse and scattered by the target enter module 702 (i.e., a distal end (light-receiving) surface of the light-receiving optical conduit of a detector 706). Detectors 706 of a module 702 may be alternatively disposed on the module 702 in any other suitable way as may serve a particular implementation.

In some examples, each module 702 has a rigid construction such that the source-detector distance for all detectors 706 on the module 702 is fixed (e.g., the positions of detectors 706 on the module 702 are fixed). Additionally, in some examples the source-detector distance for all detectors 706 among all modules 702 in wearable module assembly 700 is the same. Such configuration ensures uniform coverage over the target and simplifies processing of the detected signals as compared with an uneven distribution of sources and detectors. Moreover, maintaining a known, fixed source-detector distance allows subsequent processing of the detected signals to infer spatial (e.g., depth localization, inverse modeling) information about the detected signals. A fixed, uniform source-detector spacing also provides consistent spatial (lateral and depth) resolution across the target area of interest, e.g., brain tissue.

In some configurations, a module 702 may be formed with a curve along one or more axes. For example, a module 702 may be slightly curved along two perpendicular axes, thereby improving contact of light source 704 and detectors 706 with a curved surface (e.g., the head) of the user's body. Additionally, the curved construction of module 702 may help prevent loss of contact between light source 704 and detectors 706 due to other forces acting on the module 702, such as pulling by cords, wires, or optical fibers attached to the module 702, movement of the user, etc.

Wearable module assembly 700 also includes a connecting assembly 710 that physically connects individual modules 702 with one another. In some examples, connecting assembly 710 flexibly connects modules 702 such that wearable module assembly 700 is conformable to a 3D (non-planar) surface, such as a surface of the user's body (e.g., the user's head), when the wearable module assembly 700 is worn by the user. Connecting assembly 710 may be implemented by any suitable device, structure, connectors, or mechanism as may suit a particular implementation.

For example, as shown in FIG. 7, connecting assembly 710 is implemented by a plurality of connectors 712 (e.g., connectors 712-1 to 712-3) between adjacent modules 702. Connectors 712 may be implemented by any suitable connecting mechanisms that flexibly connect adjacent modules 702, such as hinges, flexible straps (e.g., elastic bands, fabric straps, cords, etc.), ball joints, universal joints, snap-fit connections, and the like.

In some examples, connectors 712 may be attached to modules 702 at mutually-facing side surfaces of modules 702. Additionally or alternatively, connectors 712 may be attached to each module 702 at front surfaces 708 and/or on back surfaces of modules 702 (e.g., surfaces facing away from the body of the user when wearable module assembly 700 is worn by the user). Connectors 712 may be attached to modules 702 in any suitable way, such as by fasteners (e.g., screws), adhesion, magnets, hook-and-loop, snap-fit connections, and any other suitable attachment mechanism. In some examples, a module 702 may be removably attached to connectors 712 such that the module 702 may be easily attached to and/or removed from wearable assembly 700. In some examples, connectors 712 are integrally formed with modules 702 (e.g., with housings of modules 702).

Connectors 712 may permit movement of a module 702 relative to an adjacent, connected module 702 in one or more degrees of freedom. For instance, a hinge connector may enable movement (rotation) of a module 702 about a single axis that is parallel to adjacent, facing edges of modules 702. A flexible strap may provide up to three degrees of translational movement and/or up to three degrees of rotational movement of a module 702 relative to an adjacent, connected module 702.

In some examples, connecting assembly 710 (e.g., connectors 712) prohibits translational movement of modules 702 toward/away from one another to thereby maintain a substantially uniform spacing of all adjacent modules 702 as well as a uniform spacing of light sources 704 and detectors 706. In such configurations, the spacing between a light source 704 on a first module and detectors 706 that are positioned at similar positions on all adjacent modules may be maintained at a fixed, uniform distance. For example, the source-detector distance between light source 704-1 and detectors 706-24 and 706-33 is the same fixed distance, and the source-detector distance between light source 704-1 and detectors 706-23, 706-25, 706-32, 706-34 is the same fixed distance.

Figure 8:
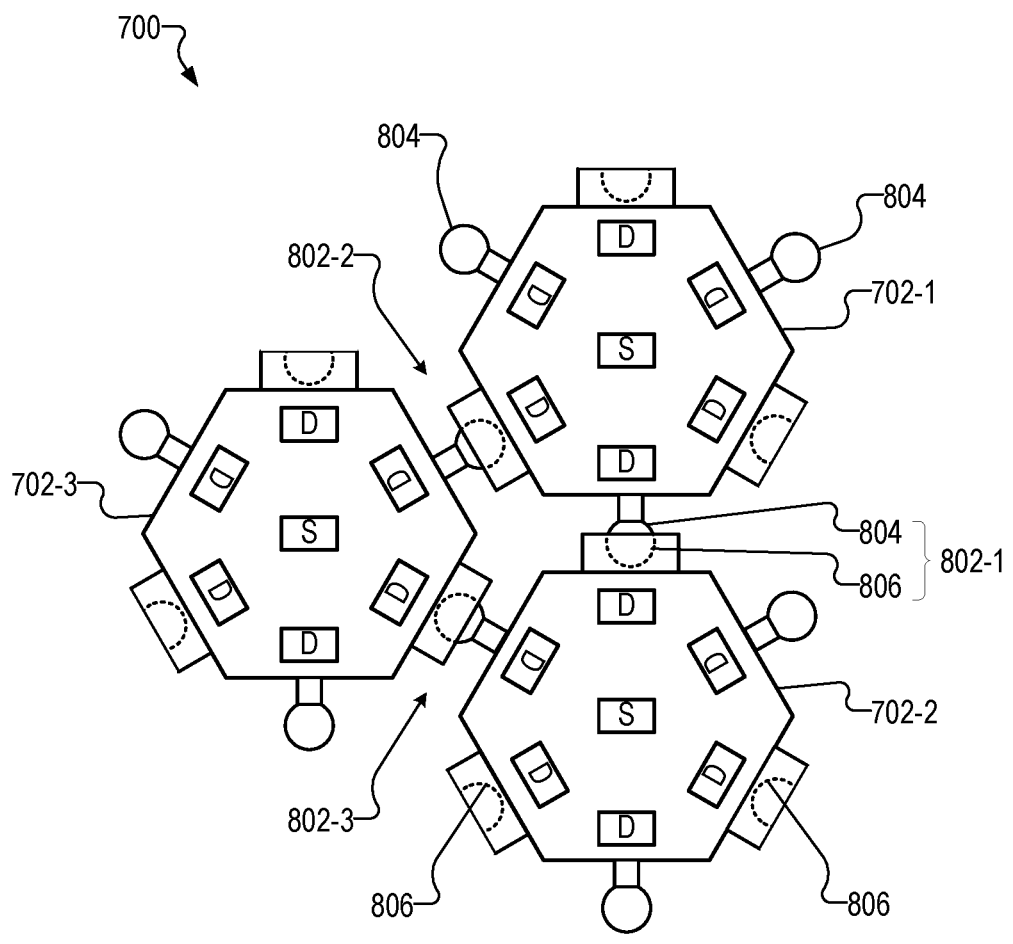
FIG. 8 illustrates an exemplary implementation of a wearable module assembly.

FIG. 8 illustrates an exemplary implementation of wearable module assembly 700. FIG. 8 is similar to FIG. 7 except that connectors 712 are depicted as ball joints 802. As shown, each module 702 includes three bearing studs 804 and three sockets 806 arranged on alternate side surfaces of the module 702. However, the module 702 may include any other number and arrangement of bearing studs 804 and sockets 806 as may serve a particular implementation or geometric configuration of modules 702. Moreover, while FIG. 8 shows that sockets 806 are formed in a casing that protrudes from the side surfaces, sockets 806 may alternatively be formed inside the side surfaces such that they do not protrude from the side surfaces.

A ball joint 802 is formed when a bearing stud 804 of a module 702 is inserted into an adjacent socket 806 of an adjacent module 702. For example, First module 702-1 is connected to second module 702-2 by a ball joint 802-1 and is connected to third module 702-3 by a ball joint 802-2, and second module 702-2 is connected to third module 702-3 by a ball joint 802-3. While FIG. 8 shows that bearing studs 804 are inserted into sockets 806 in a direction that is perpendicular to the side surfaces of modules 702, sockets 806 may alternatively be configured to receive bearing studs 804 in a direction that is parallel to the side surfaces of modules 702. In this way modules 702 can easily be inserted into and removed from wearable module assembly 700.

Each ball joint 802 provides three degrees of rotational freedom, thereby enabling wearable module assembly 700 to bend and flex as necessary to conform to a 3D surface. Additionally, ball joints 802 restrict translational movement of modules 702 relative to one another, thereby maintaining the spacing between adjacent modules 702 and thus maintaining substantial uniformity in the spacing of light sources 704 and detectors 706 throughout wearable module assembly 700. In alternative examples, bearing studs 804 and/or sockets 806 may be movably mounted on modules 702, such as with springs, bearing studs, etc., to thereby enable translational movement of modules 702.

In the configurations described above, connecting assembly 710 is implemented by a plurality of individual connectors 712 that directly connect adjacent modules 702. In alternative configurations, connecting assembly 710 may be a common support assembly that indirectly connects modules 702. That is, modules 702 are not directly connected to one another but are connected to a common support assembly that holds each individual module 702 in a substantially fixed position relative to the other modules 702. In this way the common support assembly maintains uniform module spacing and source-detector spacing through wearable module assembly 700.

Figure 9A:
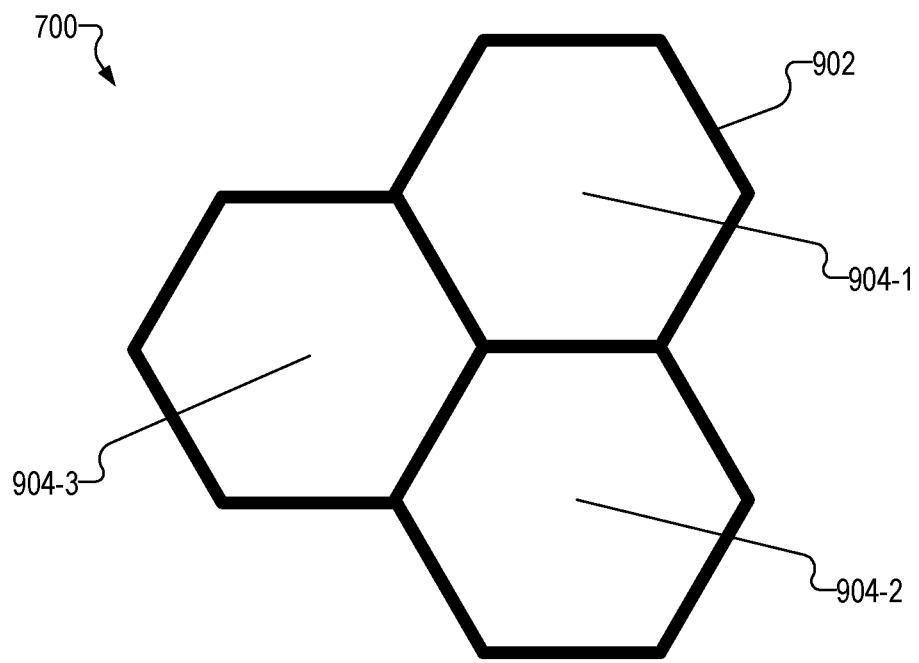
FIGS. 9A and 9B illustrate another exemplary implementation of a wearable module assembly.
Figure 9B:
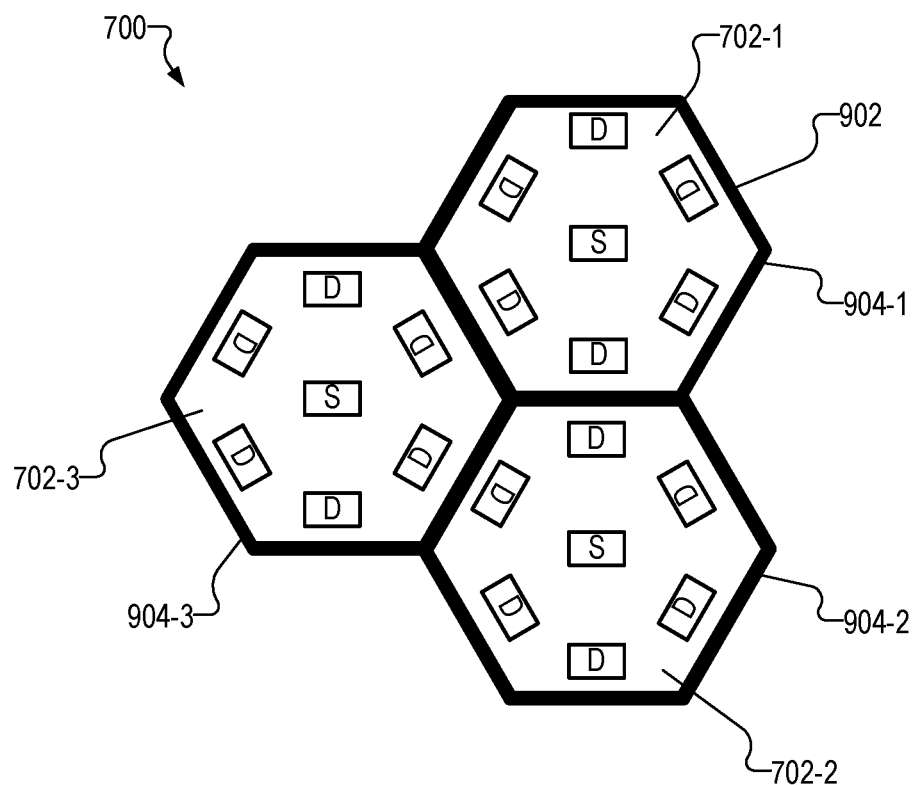

FIGS. 9A and 9B illustrate an exemplary implementation of wearable module assembly 700 incorporating a common connecting assembly. FIGS. 9A and 9B are similar to FIG. 7 except that modules 702 are connected by a common connecting assembly 902. Connecting assembly 902 includes individual positions 904 (e.g., positions 904-1 through 904-3) in which individual modules 702 are configured to be inserted and attached to connecting assembly 902. FIG. 9A shows connecting assembly 902 before modules 702 have been inserted into respective positions 904, and FIG. 9B shows connecting assembly 902 with individual modules 702 inserted into respective positions 904.

In some examples, connecting assembly 902 includes an open-mesh structure in which individual positions 904 are openings in the open-mesh structure. As shown in FIG. 9B, individual modules 702 may be inserted into respective positions 904 and held in place by the mesh structure. The mesh structure may be formed of any suitable flexible, rigid, and/or semi-rigid material as may serve a particular implementation (e.g., cord, fiber, wire, bands, straps, yard, etc.). In some examples, the mesh structure is formed of an elastic material and the openings of positions 904 are smaller than modules 702. When modules 702 are inserted into positions 904, the elastic tension of the mesh securely holds modules 702 in place. In some examples, each module 702 may include a groove around the side surfaces of the module 702 and in which the mesh structure may rest without slipping and sliding off the module 702. The open-mesh structure of connecting assembly 902 facilitates insertion and removal of individual modules 702 in/from wearable module assembly 700.

Alternatively to an open mesh-structure, connecting assembly 902 may include a substantially closed-surface structure. That is, individual positions 904 are not openings in the structure but rather are locations on a surface of a support substrate or material. Connecting assembly 902 may be formed of any flexible, rigid, or semi-rigid material as may suit a particular implementation. In some examples, connecting assembly 902 is implemented by a flex circuit onto which each individual module 702 may be physically attached (and electrically connected). In additional or alternative examples, connecting assembly 902 is implemented by a headgear, such as a hat, a helmet, or a headband (see, for example, FIGS. 15-20).

Modules 702 may be attached to a closed-surface connecting assembly 902 in any suitable way, such as by a fastener, adhesive, snap-on attachment, hook-and-loop fastener, and/or any other suitable attachment mechanism. Modules 702 may be attached to connecting assembly 902 at the front surface 708 or at the back surface (not shown) of modules 702.

In some examples, positions 904 are surrounded by a wall such that, when modules 702 are inserted into their respective individual positions 904, the walls physically separate modules 702 one from another. In alternative embodiments, a module (e.g., module 702-1) may be in at least partial physical contact with a neighboring module (e.g., module 702-2).

In some examples, connecting assembly 902 may be preconfigured to conform to a shape of the user's body on which wearable module assembly 700 will be worn. For example, connecting assembly 902 may be formed in the shape of headgear to be worn on a user's head (see, for example, FIGS. 15-20).

In the various wearable module assemblies 700 described above, one or more modules 702 may be removable. Thus, a size and configuration of a wearable module assembly 700 may be adjusted as desired, even while the wearable module assembly 700 is worn by the user. Such modular configurations of wearable module assembly 700 can be used to customize the fit of the wearable module assembly 700. For example, one or more modules 702 may be added to or removed from wearable module assembly 700 depending on where the wearable module assembly 700 will be worn by the user (e.g., the head, the chest, etc.) and/or depending on the size of the user. For instance, one or more modules 702 may be removed from wearable module assembly 700 when wearable module assembly 700 will be worn by a child, and one or more modules 702 may be added when wearable module assembly will be worn by an adult. Additionally, modules 702 may be added or removed as necessary to ensure complete coverage of a region of interest. In some examples, the region of interest is a particular functional region of the brain, such as the cerebrum, the cerebellum, the cerebral cortex, a particular lobe (e.g., frontal lobe, parietal lobe, occipital lobe, temporal lobe, anterior lobe, posterior lobe, flocculonodular lobe, etc.) or a particular area within a lobe or other brain region (e.g., Wernicke's Area, Broca's Area, prefrontal cortex, the visual area, the motor function area, etc.). The wearable module assembly 700 may be configured to entirely cover the particular functional region of the brain so that the entire functional region of the brain is imaged by the optical measurement system.

In some examples, wearable module assembly 700 may include, in addition to or in place of a module 702, an auxiliary module having a different operating modality than modules 702. For instance, the auxiliary module may be configured to detect biological signals from the target by a modality that is different from a modality of the plurality of wearable modules. As mentioned above, modules 702 are configured to operate in a time domain-based optical measurement modality (e.g., TD-NIRS). An operating modality of the auxiliary module may include, for example, continuous wave NIRS (CW-NIRS), frequency-domain NIRS (FD-NIRS), electroencephalography (EEG), electromyography (EMG), magnetoencephalography (MEG), positron emission tomography (PET), functional magnetic resonance imaging (fMRI), single-photon emission computed tomography (SPECT), functional ultrasound imaging (fUS), and any other imaging modality as may serve a particular implementation. For example, an auxiliary module may include recording metal electrodes used in EEG, needle electrodes used in EMG, or magnetometers used in MEG.

The auxiliary module may be physically and flexibly connected to modules 702 by way of the connecting assembly (e.g., connecting assembly 710 or 902). With the modular configurations described herein, the auxiliary module may be easily added to or removed from wearable module assembly 700 when desired, and the auxiliary operating modality may operate simultaneously or in conjunction with the time domain-based optical measurement modality of modules 702.

Module assembly 700 may also include "dummy" modules that may be added to wearable module assembly 700 to help maintain appropriate spacing and pressure on the user's body. Dummy modules may have the same shape and/or weight as modules 702 but do not provide any imaging functionality. In some examples, dummy modules may serve other non-imaging purposes, such as measuring a tension on connecting assembly 710 or 902, measuring pressure on the user's body, or any other desired auxiliary function. In some examples, a processing unit of optical measurement system 100 may be included, entirely or in part, in a dummy module.

In some examples, the connecting assembly 710 or connecting assembly 902 may electrically connect any two or more modules 702 and/or connect a module 702 to other components of optical measurement system 100. For example, connectors 712 (e.g., ball joints 802) may be electrically conductive to thereby electrically connect components in connected modules 702 to one another and/or to a common power source and/or data bus. In some examples, connectors 712 are implemented by ribbon cables that physically, flexibly, and electrically connect modules 702. In other examples, connecting assembly 902 is implemented by a flex circuit that connects electrical components in each module 702 to a common power source and/or data bus.

As shown in FIGS. 7-9B, modules 702 are depicted as having a housing with a surface (e.g., front surface 708) and a substantially hexagonal shape. Accordingly, connecting assembly 710 or 902 may connect modules 702 edge-to-edge in a honeycomb-type arrangement. Such arrangement enables sufficient flexure of wearable module assembly 700 to conform to a surface of a body of the user. To further enable flexure of wearable module assembly 700, modules 702 may have rounded or beveled edges and corners, thereby permitting a tighter spacing of modules 702 while allowing sufficient movement of modules 702 relative to one another. Additionally or alternatively, connecting assembly 902 may maintain a gap between adjacent modules 702 to further allow sufficient movement of modules 702 and flexure of wearable module assembly 700.

Figure 10:
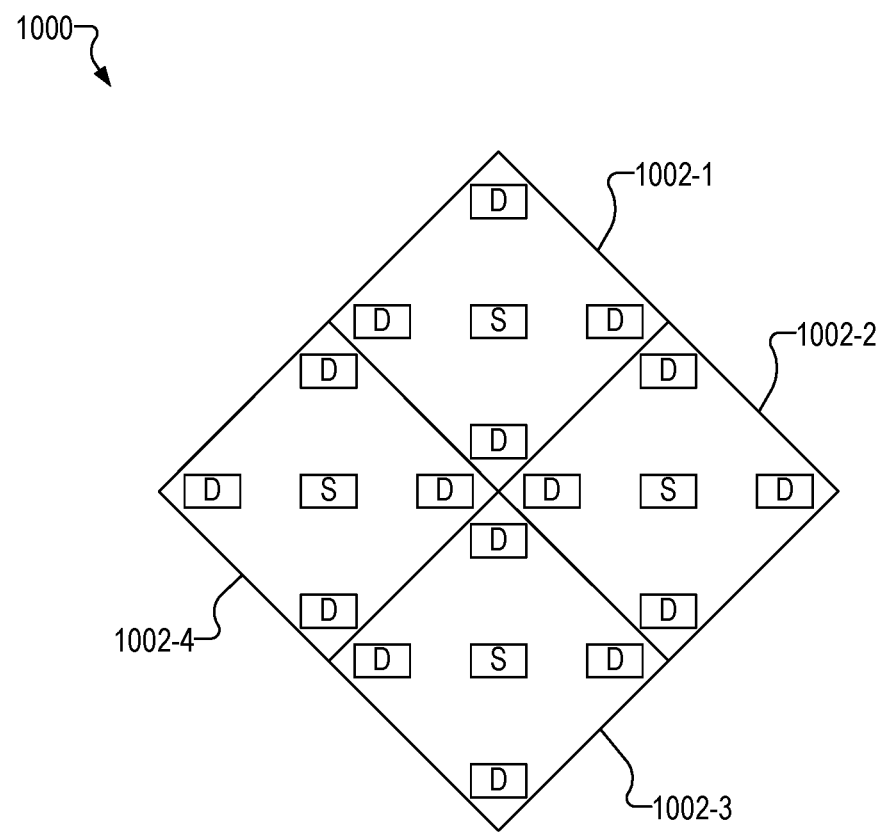
FIGS. 10-12 illustrate various other exemplary implementations of a wearable module assembly.

Modules 702 are not limited to a hexagonal geometry, but may additionally or alternatively have any other suitable geometry (e.g., in the shape of a pentagon, octagon, square, rectangle, circle, triangle, free-form, a combination of shapes, etc.) as may serve a particular implementation. FIG. 10 shows another illustrative wearable module assembly 1000 having a plurality of modules 1002 (e.g., modules 1002-1 through 1002-4) that are each in the shape of a diamond. Modules 1002 may be connected to one another by any of the connecting assemblies described herein. While four modules 1002 are shown to be included in wearable module assembly 1000, in alternative configurations, any number of modules 1002 (e.g., a single module up to sixteen or more modules) may be included in wearable module assembly 1000.

Figure 11:
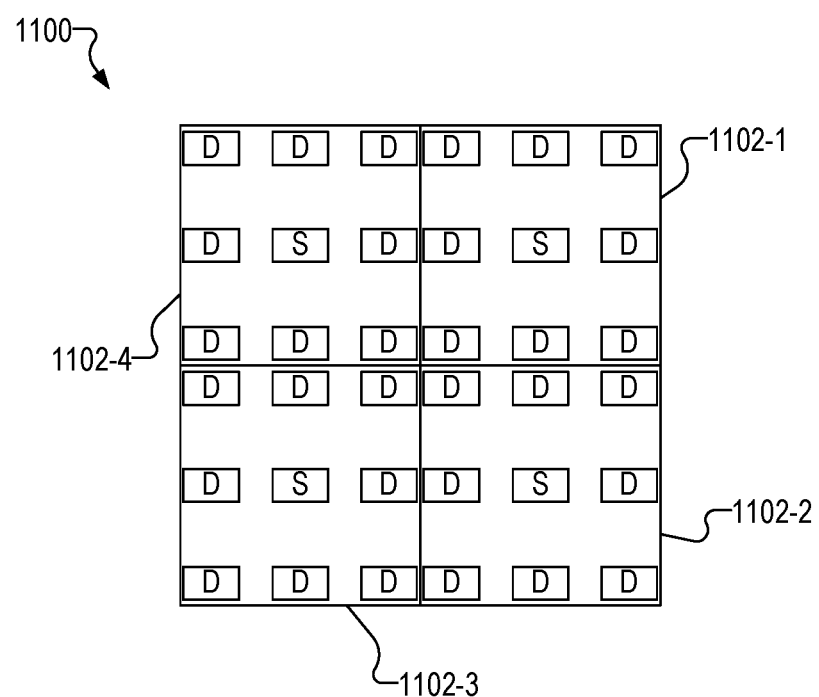

FIG. 11 shows another illustrative wearable module assembly 1100 having a plurality of modules 1102 (e.g., modules 1102-1 through 1102-4) that are each in the shape of a square. Modules 1102 may be connected to one another by any of the connecting assemblies described herein. While four modules 1102 are shown to be included in wearable module assembly 1100, in alternative configurations, any number of modules 1102 (e.g., a single module up to sixteen or more modules) may be included in wearable module assembly 1100.

Figure 12:
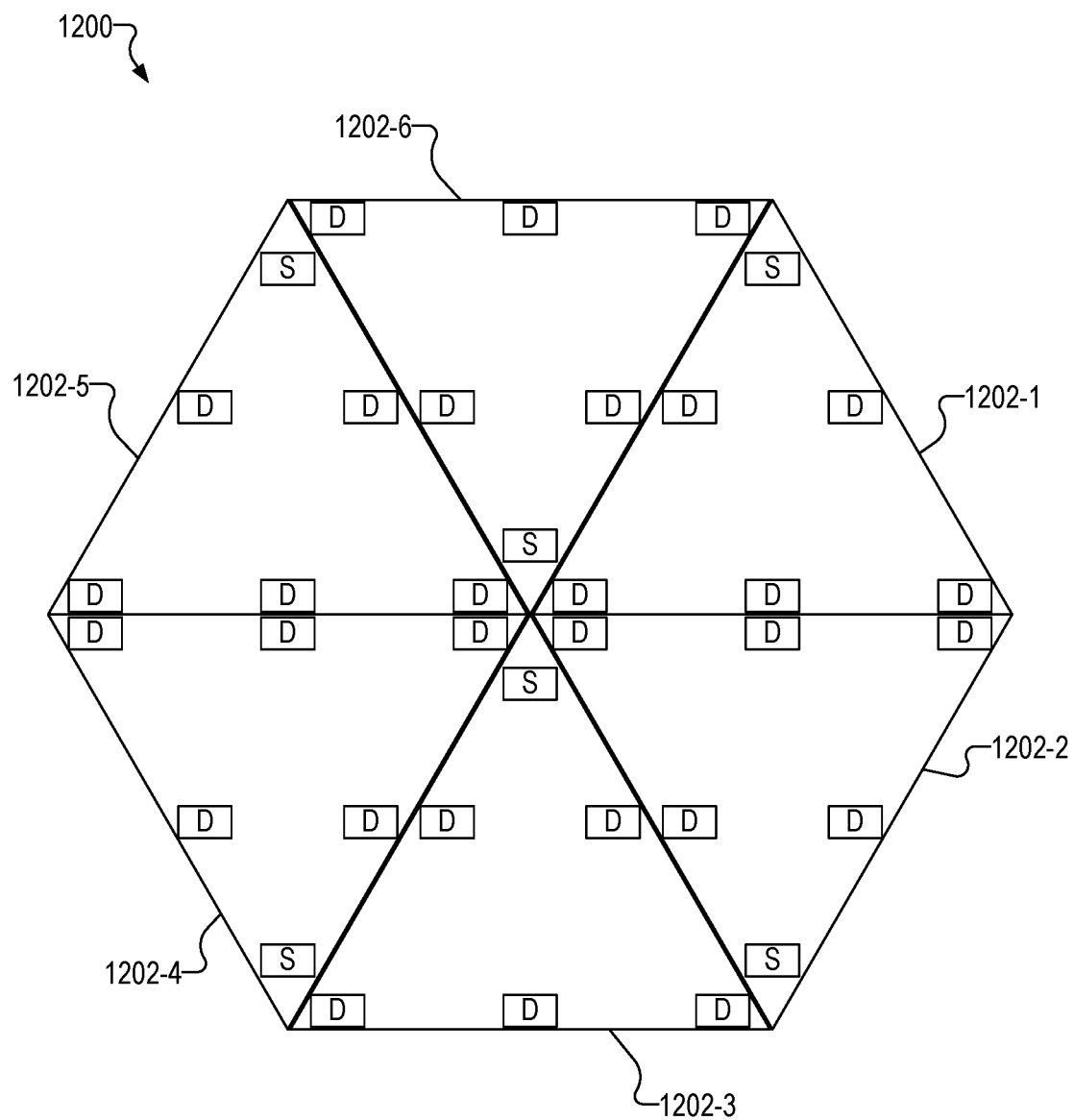

FIG. 12 shows another illustrative wearable module assembly 1200 having a plurality of modules 1202 (e.g., modules 1202-1 through 1202-6) that are each in the shape of a triangle. Modules 1202 may be connected to one another by any of the connecting assemblies described herein. While six modules 1202 are shown to be included in wearable module assembly 1200, in alternative configurations, any number of modules 1202 (e.g., a single module up to sixteen or more modules) may be included in wearable module assembly 1200.

Figure 13A:
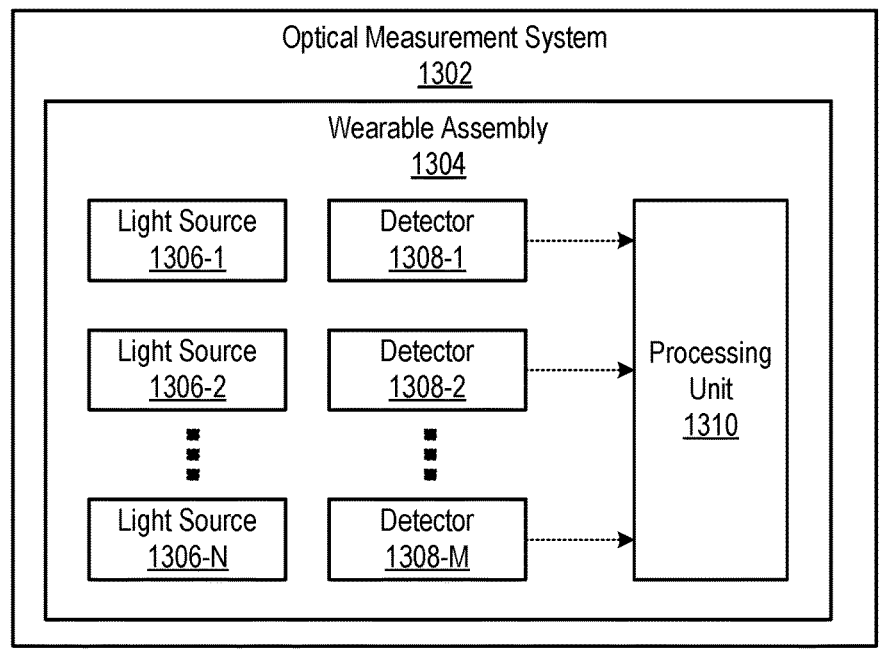
FIGS. 13A and 13B illustrate exemplary configurations of an exemplary optical measurement system that includes a processing unit.
Figure 13B:
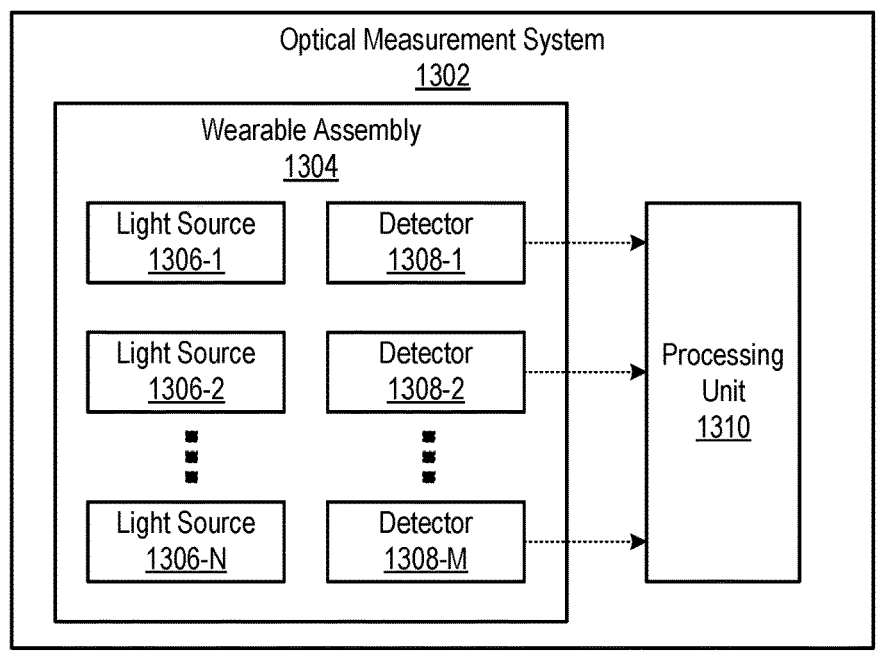

In some examples, optical measurement systems described herein (e.g., optical measurement system 100) may include a processing unit configured to perform one or more operations based on photon arrival times detected by the detectors described herein. For example, FIGS. 13A-13B show illustrative configurations 1300-1 and 1300-2 of an exemplary optical measurement system 1302 in accordance with the principles described herein.

Optical measurement system 1302 may be an implementation of optical measurement system 100 and, as shown, includes a wearable assembly 1304, which includes N light sources 1306 (e.g., light sources 1306-1 through 1306-N) and M detectors 1308 (e.g., detectors 1308-1 through 1308-M). Optical measurement system 1302 may include any other components as may serve a particular implementation.

Wearable assembly 1304 may be implemented by any of the wearable devices, wearable modules, wearable assemblies (e.g., wearable assembly 600), wearable module assemblies (e.g., wearable module assembly 700), and/or wearable units described herein. For example, wearable assembly 1304 may be implemented by a wearable device configured to be worn on a user's head. Wearable assembly 1304 may additionally or alternatively be configured to be worn on any other part of a user's body. In some examples, optical measurement system 1302 may include a plurality of wearable assemblies 1304.

Light sources 1306 are each configured to emit light and may be implemented by any of the light sources described herein. Detectors 1308 may each be configured to detect arrival times for photons of the light emitted by one or more light sources 1306 after the light is scattered by the target or diverted without being scattered by the target. For example, a detector 1308 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon. Detectors 1308 may be implemented by any of the detectors described herein.

In configuration 1300-1, a processing unit 1310 is also included in wearable assembly 1304 (e.g., in a housing of a module 702, in a dummy module, or in an auxiliary module). In configuration 1300-2, processing unit 1310 is not included in wearable assembly 1304 (i.e., processing unit 1310 is housed in an additional housing of a device located external to wearable assembly 1304). Either configuration 1300-1 or 1300-2 may be used in accordance with the systems, circuits, and methods described herein.

Detectors 1308 on wearable assembly 1304 may output signals representative of photon arrivals, as described herein. Processing unit 1310 is configured to receive the output signals and perform one or more operations based on the signals. For example, processing unit 1310 may generate measurement data (e.g., one or more histograms) based on the signals, as described herein.

As mentioned, in configuration 1300-2, processing unit 1310 is not included in wearable assembly 1304. For example, processing unit 1310 may be included in a wearable device separate from wearable assembly 1304. To illustrate, processing unit 1310 may be included in a wearable device configured to be worn off the head (e.g., on a belt) while wearable assembly 1304 is worn on the head. In these examples, one or more communication interfaces (e.g., cables, wireless interfaces, etc.) may be used to facilitate communication between wearable assembly 1304 and the separate wearable device.

Additionally or alternatively, in configuration 1300-2, processing unit 1310 may be remote from the user (i.e., not worn by the user). For example, processing unit 1310 may be implemented by a stand-alone computing device communicatively coupled to wearable assembly 1304 by way of one or more communication interfaces (e.g., cables, wireless interfaces, etc.).

In some examples, processing unit 1310 may be distributed between multiple devices and/or multiple locations as may serve a particular implementation. Processing unit 1310 may be implemented by processor 108, controller 112, control circuit 204, and/or any other suitable processing and/or computing device or circuit.

Figure 14:
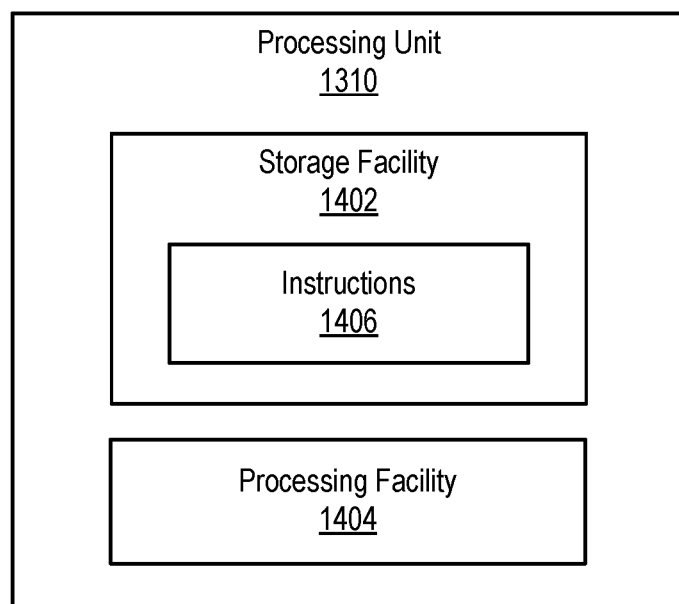
FIG. 14 illustrates an exemplary implementation of the processing unit of FIGS. 13A and 13B.

For example, FIG. 14 illustrates an exemplary implementation of processing unit 1310 in which processing unit 1310 includes a memory (storage facility) 1402 and a processor (processing facility) 1404 configured to be selectively and communicatively coupled to one another. In some examples, memory 1402 and processor 1404 may be distributed between multiple devices and/or multiple locations as may serve a particular implementation.

Memory 1402 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1402 may maintain (e.g., store) executable data used by processor 1404 to perform one or more of the operations described herein. For example, memory 1402 may store instructions 1406 that may be executed by processor 1404 to perform any of the operations described herein. Instructions 1406 may be implemented by any suitable application, program (e.g., sound processing program), software, code, and/or other executable data instance. Memory 1402 may also maintain any data received, generated, managed, used, and/or transmitted by processor 1404.

Processor 1404 may be configured to perform (e.g., execute instructions 1406 stored in memory 1402 to perform) various operations described herein. For example, processor 1404 may be configured to perform any of the operations described herein as being performed by processing unit 1310.

FIGS. 15-20 illustrate embodiments of a wearable device 1500 that includes elements of the optical measurement systems and/or wearable assemblies described herein. In particular, the wearable devices 1500 include a plurality of modules 1502, similar to modules 700 described herein. For example, each module 1502 includes a light source 704 and a plurality of detectors 706. Light source 704 may be implemented by or be similar to one or more light sources described herein (e.g., light source 110, light source 602, etc.). Each detector 706 may implement or be similar to one or more detectors or detector assemblies described herein (e.g., detector 104) and may include a plurality of photodetectors. The wearable devices 1500 may each also include a controller (e.g., controller 112) and a processor (e.g., processor 108) and/or be communicatively connected to a controller and/or a processor. In general, wearable device 1500 may be implemented by any suitable headgear and/or clothing article configured to be worn by a user. The headgear and/or clothing article may include batteries, cables, and/or other peripherals for the components of the optical measurement systems described herein. In some examples, the headgear includes one or more modules 1502. Additionally or alternatively, modules 1502 are included in or implemented by modules 700.

Figure 15:
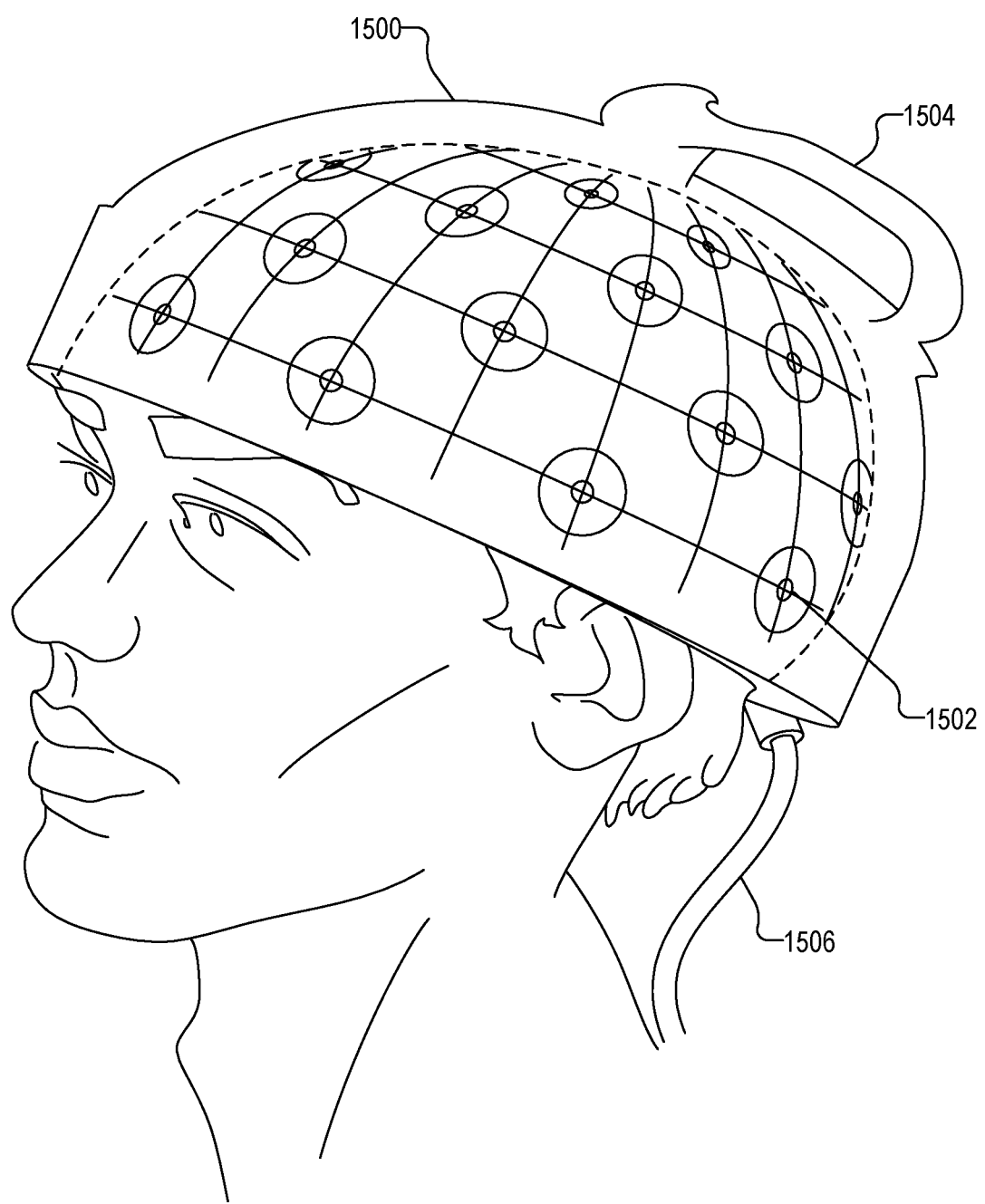
FIGS. 15-20 illustrate embodiments of a wearable device that includes elements of the optical detection systems described herein.
Figure 16:
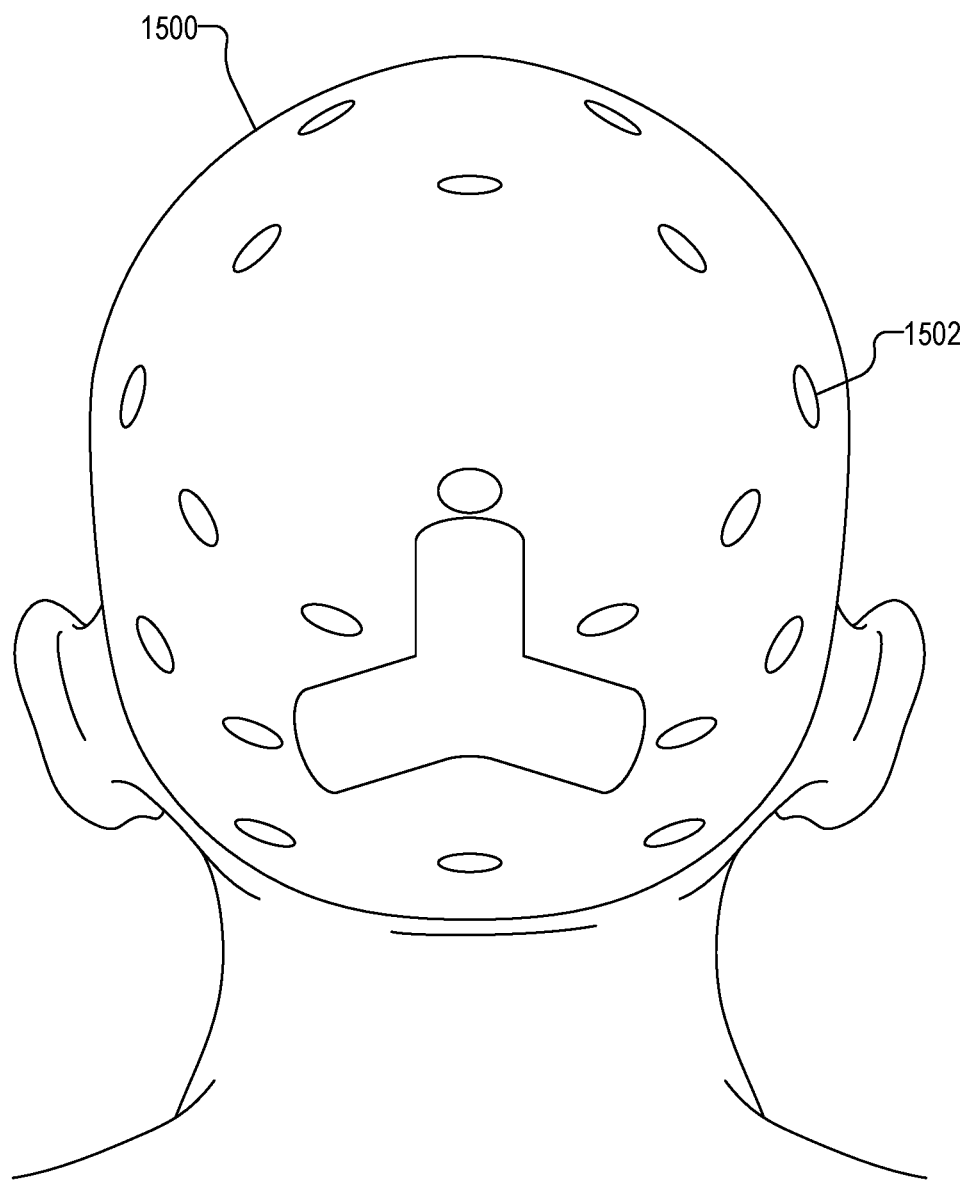
Figure 17:
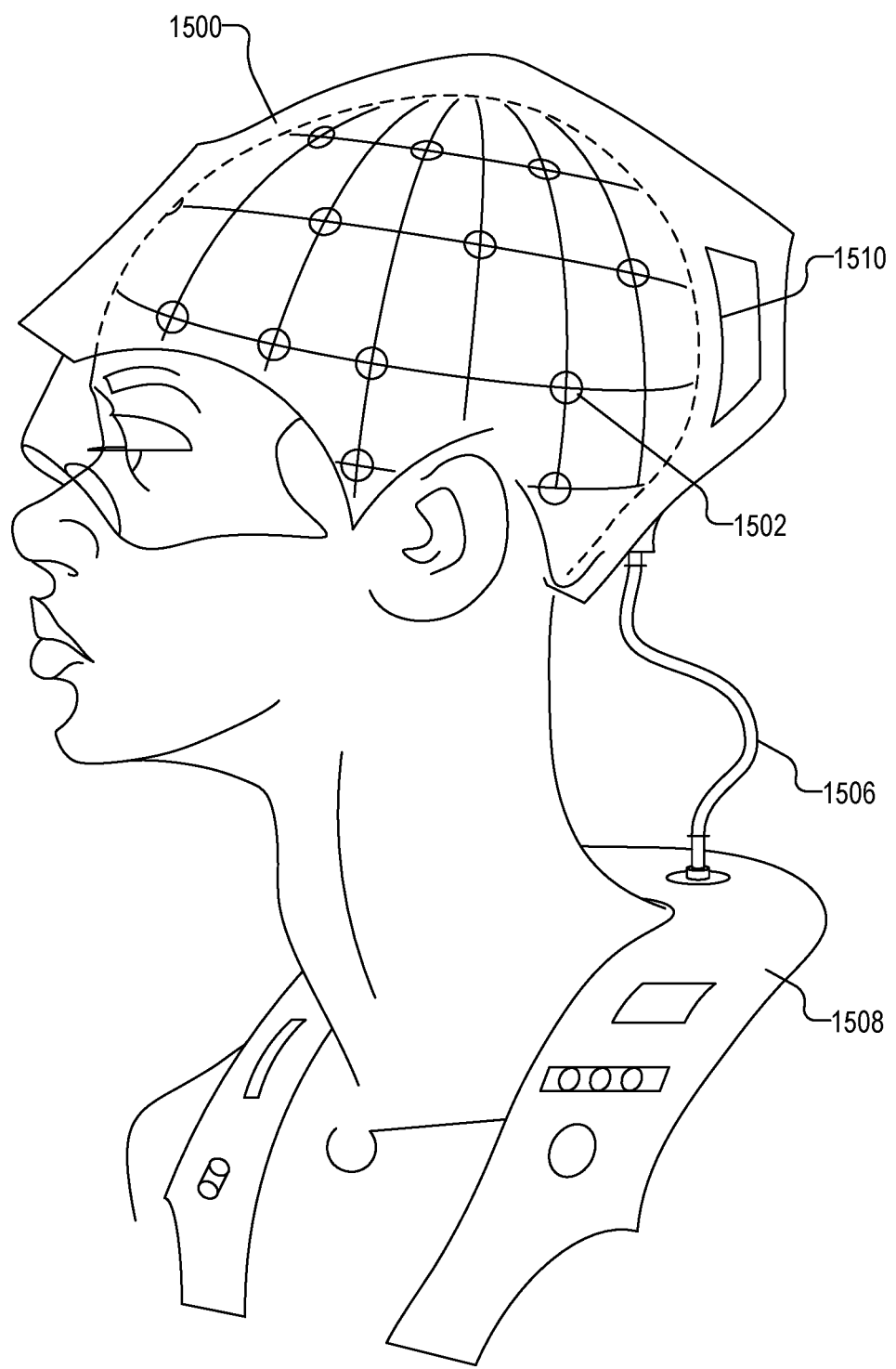

FIG. 15 illustrates an embodiment of a wearable device 1500 in the form of a helmet with a handle 1504. A cable 1506 extends from the wearable device 1500 for attachment to a battery or hub (with components such as a processor or the like). FIG. 16 illustrates another embodiment of a wearable device 1500 in the form of a helmet showing a back view. FIG. 17 illustrates a third embodiment of a wearable device 1500 in the form of a helmet with the cable 1506 leading to a wearable garment 1508 (such as a vest or partial vest) that can include a battery or a hub (e.g., processing unit 1310). Alternatively or additionally, the wearable device 1500 can include a crest 1510 or other protrusion for placement of the hub or battery.

Figure 18:
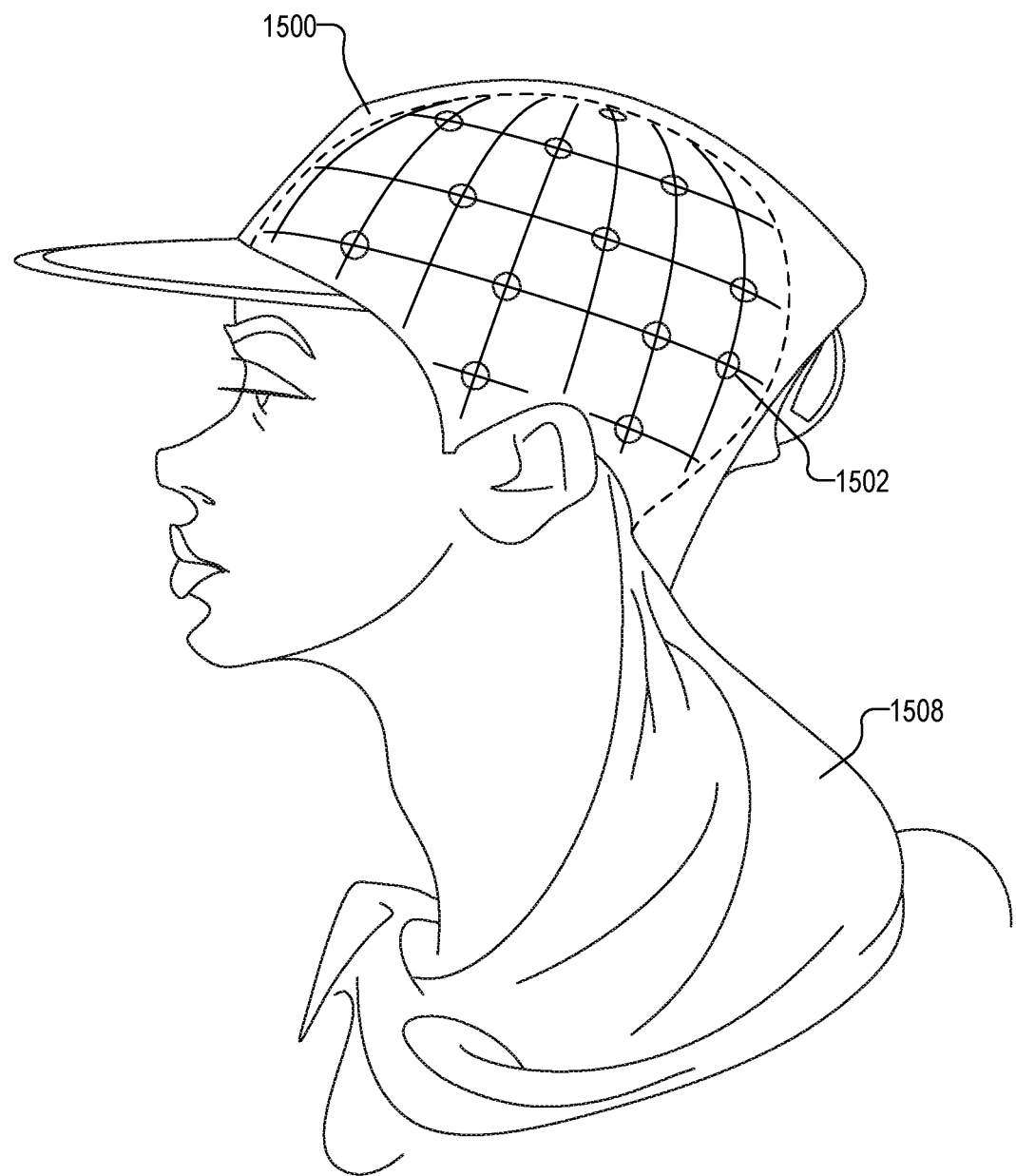
Figure 19:
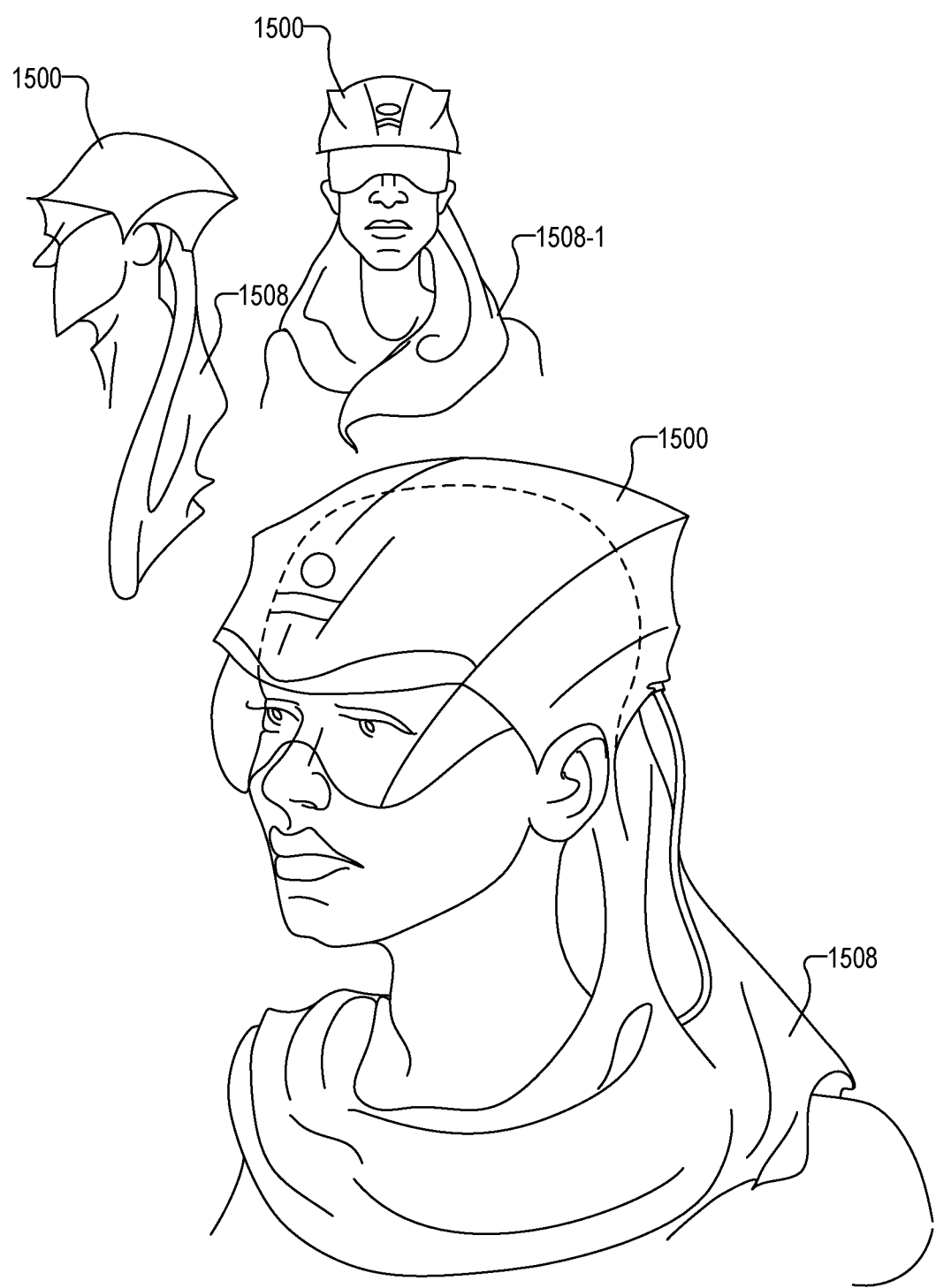
Figure 20:
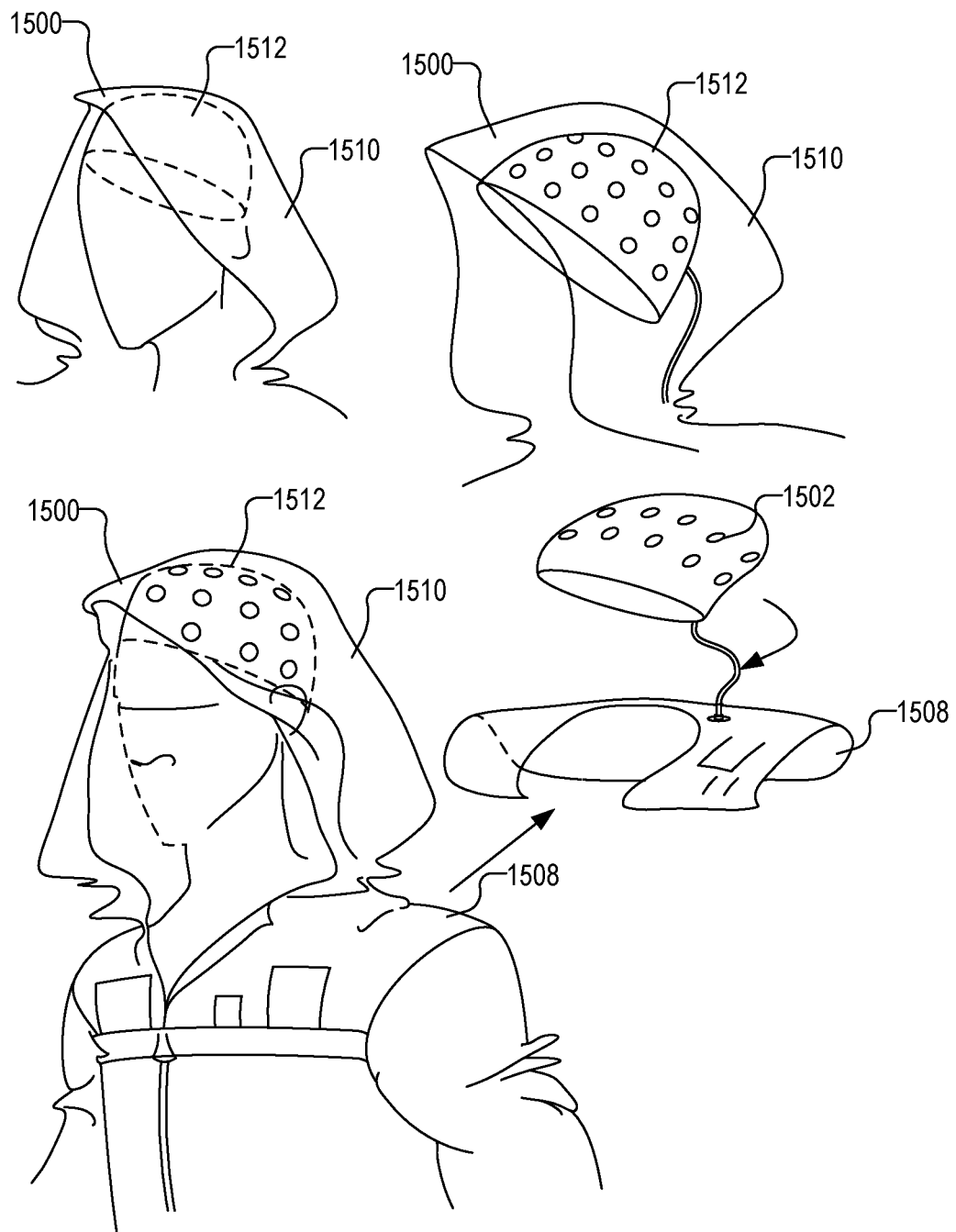

FIG. 18 illustrates another embodiment of a wearable device 1500 in the form of a cap with a wearable garment 1508 in the form of a scarf that may contain or conceal a cable, battery, and/or hub. FIG. 19 illustrates additional embodiments of a wearable device 1500 in the form of a helmet with a one-piece scarf 1508 or two-piece scarf 1508-1. FIG. 20 illustrates an embodiment of a wearable device 1500 that includes a hood 1510 and a beanie 1512 which contains the modules 1502, as well as a wearable garment 1508 that may contain a battery or hub.

In some examples, a wearable assembly (e.g., wearable module assembly 700) may include a pressing member configured to press the plurality of wearable modules toward the surface of the body of the user when the wearable module assembly is worn on the body of the user. Thus, the pressing member may help maintain contact of the light sources (e.g., light sources 704) and detectors (e.g., detector 706) with the body surface. The pressing member may include, for example, an elastic band, a strap, a hat, an inflatable bag within a helmet, or any other suitable device configured to press the wearable assembly against the body surface. For instance, the helmets shown in FIGS. 15 and 16 may cover wearable module assembly 700 and be configured to press modules 702 against the user's head. In some examples the fit of the helmets is adjustable to produce the pressing force. Alternatively, the helmets may include an inflatable airbag that presses wearable module assembly 700 against the user's head.

Figure 21:
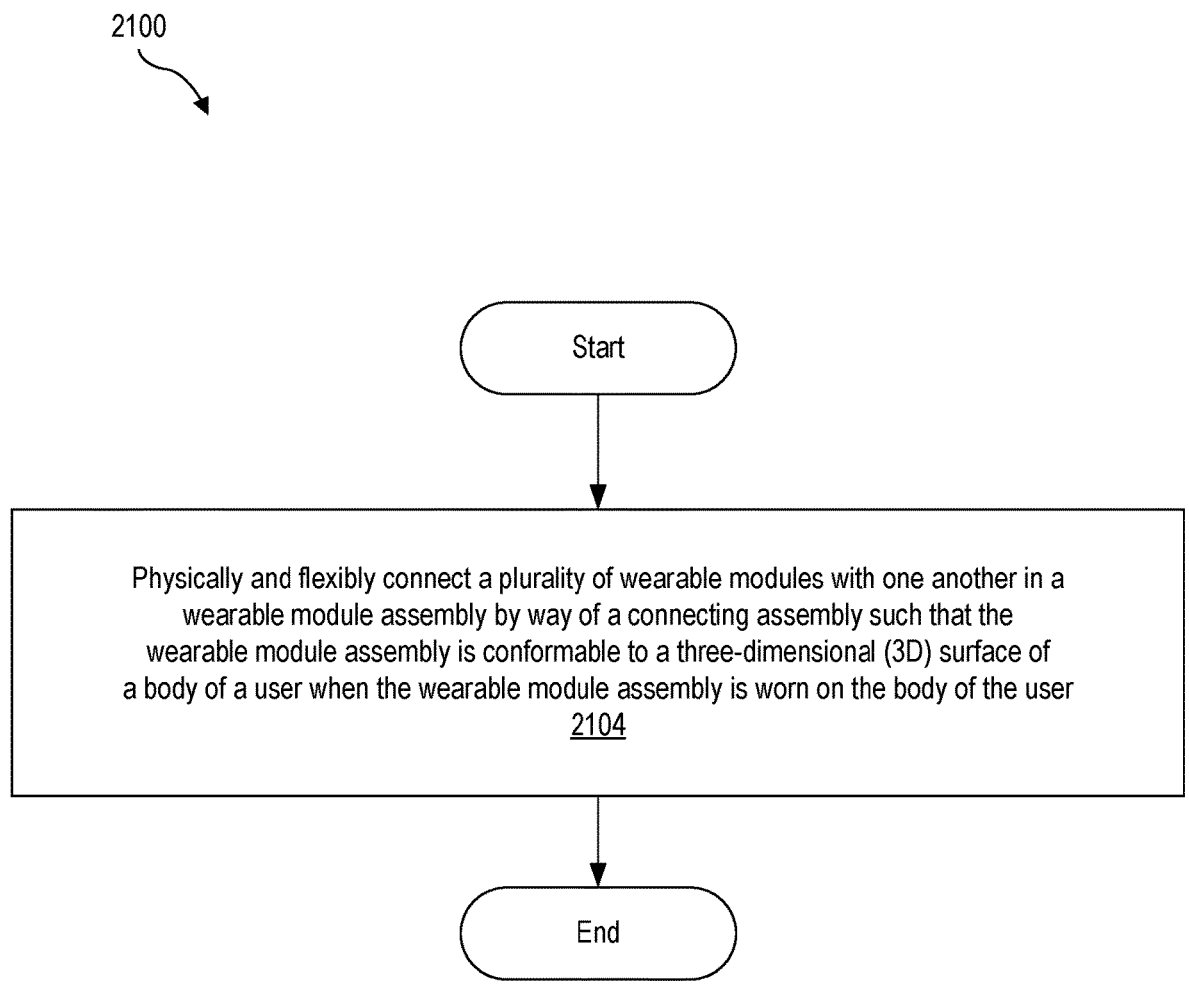
FIG. 21 illustrates an exemplary method.

FIG. 21 illustrates an exemplary method 2100. While FIG. 21 illustrates exemplary steps according to one embodiment, other embodiments may omit, add to, reorder, and/or modify any of the steps shown in FIG. 21.

In step 2102, a plurality of wearable modules are physically and flexibly connected with one another in a wearable module assembly by way of a connecting assembly such that the wearable module assembly is conformable to a three-dimensional (3D) surface of a body of a user when the wearable module assembly is worn on the body of the user. The wearable modules may be implemented by any wearable modules described herein (e.g., modules 702). The connecting assembly may be implemented by any connecting assembly described herein (e.g., connecting assembly 710 or connecting assembly 902). Operation 2102 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 22:
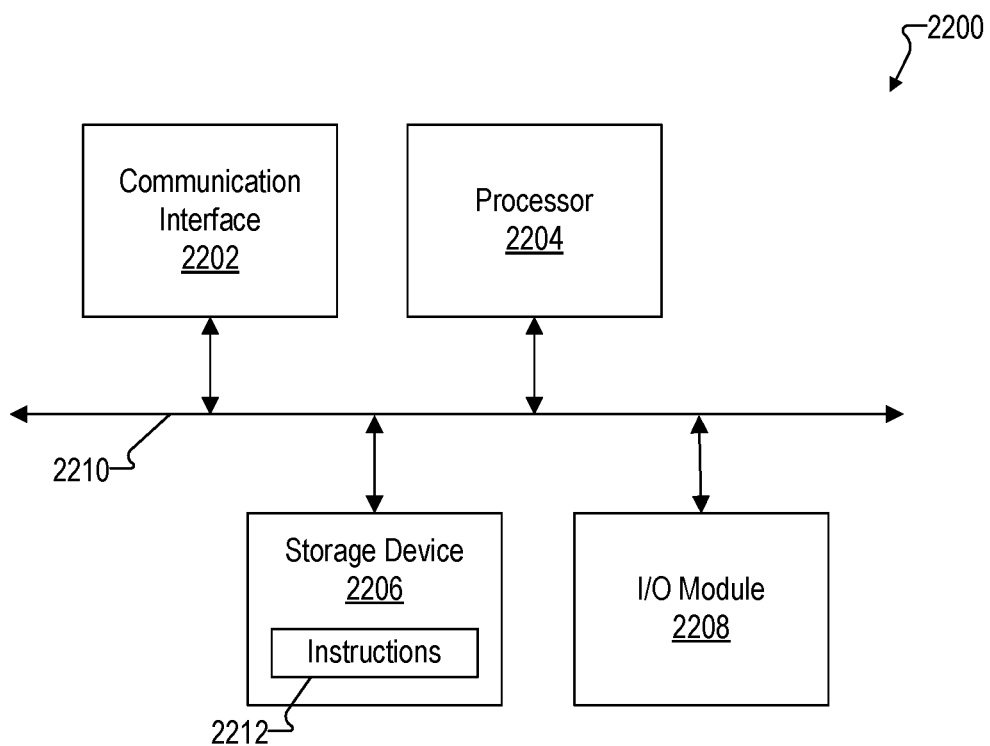
FIG. 22 illustrates an exemplary computing device.

FIG. 22 illustrates an exemplary computing device 2200 that may be specifically configured to perform one or more of the processes described herein. Any of the systems, units, computing devices, and/or other components described herein may be implemented by computing device 2200.

As shown in FIG. 22, computing device 2200 may include a communication interface 2202, a processor 2204, a storage device 2206, and an input/output ("I/O") module 2208 communicatively connected one to another via a communication infrastructure 2210. While an exemplary computing device 2200 is shown in FIG. 22, the components illustrated in FIG. 22 are not intended to be limiting. Additional or alternative components may be used in other embodiments. Components of computing device 2200 shown in FIG. 22 will now be described in additional detail.

Communication interface 2202 may be configured to communicate with one or more computing devices. Examples of communication interface 2202 include, without limitation, a wired network interface (such as a network interface card), a wireless network interface (such as a wireless network interface card), a modem, an audio/video connection, and any other suitable interface.

Processor 2204 generally represents any type or form of processing unit capable of processing data and/or interpreting, executing, and/or directing execution of one or more of the instructions, processes, and/or operations described herein. Processor 2204 may perform operations by executing computer-executable instructions 2212 (e.g., an application, software, code, and/or other executable data instance) stored in storage device 2206.

Storage device 2206 may include one or more data storage media, devices, or configurations and may employ any type, form, and combination of data storage media and/or device. For example, storage device 2206 may include, but is not limited to, any combination of the non-volatile media and/or volatile media described herein. Electronic data, including data described herein, may be temporarily and/or permanently stored in storage device 2206. For example, data representative of computer-executable instructions 2212 configured to direct processor 2204 to perform any of the operations described herein may be stored within storage device 2206. In some examples, data may be arranged in one or more databases residing within storage device 2206.

I/O module 2208 may include one or more I/O modules configured to receive user input and provide user output. I/O module 2208 may include any hardware, firmware, software, or combination thereof supportive of input and output capabilities. For example, I/O module 2208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2208 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
a wearable module assembly configured to be worn on a body of a user comprising:
a plurality of wearable modules each comprising:
a light source configured to emit a light pulse toward a target within the body of the user;
a plurality of detectors configured to receive photons included in the light pulse after the photons are scattered by the target;
a housing that houses the light source and the plurality of detectors, wherein the housing has a substantially hexagonal surface that is substantially parallel to the surface of the body of the user when the wearable module assembly is worn by the user; and
a connecting assembly that physically and flexibly connects the plurality of wearable modules such that the wearable module assembly is conformable to a three-dimensional (3D) surface of the body of the user when the wearable module assembly is worn on the body of the user, wherein the connecting assembly comprises a plurality of connectors configured to directly connect at mutually-facing side surfaces of the housings of adjacent wearable modules included in the plurality of wearable modules.

2. The optical measurement system of claim 1, wherein the connecting assembly physically connects the plurality of wearable modules in a honeycomb-type arrangement.

3. The optical measurement system of claim 1, wherein a module included in the plurality of wearable modules is removable from the connecting assembly.

4. The optical measurement system of claim 1, wherein the connecting assembly comprises a common support assembly configured to indirectly connect the plurality of wearable modules.

5. The optical measurement system of claim 4, wherein the common support assembly comprises a flex circuit or an open-mesh structure.

6. The optical measurement system of claim 1, wherein the plurality of connectors comprise ball joints.

7. The optical measurement system of claim 1, wherein the connecting assembly is configured to maintain a uniform spacing between adjacent wearable modules included in the plurality of wearable modules.

8. The optical measurement system of claim 1, wherein the connecting assembly is configured to electrically connect the plurality of wearable modules.

9. The optical measurement system of claim 1, wherein the plurality of detectors of a wearable module are separated from the light source of the wearable module by a fixed source-detector distance.

10. The optical measurement system of claim 9, wherein the source-detector distance is substantially the same for each wearable module included the plurality of wearable modules.

11. The optical measurement system of claim 10, wherein a distance between light sources of adjacent wearable modules included in the plurality of wearable modules is substantially uniform.

12. The optical measurement system of claim 1, wherein each light source comprises a plurality of laser diodes.

13. The optical measurement system of claim 1, wherein each detector comprises a plurality of single-photon avalanche diode (SPAD) circuits.

14. The optical measurement system of claim 1, further comprising a processing circuit configured to:
determine a temporal distribution of the photons detected by one or more detectors; and
generate a histogram based on the temporal distribution of the photons.

15. The optical measurement system of claim 14, wherein: the processing circuit is housed in a housing of a wearable module included in the plurality of wearable modules.

16. The optical measurement system of claim 14, wherein:
each wearable module further comprises a housing that houses the light source and the plurality of detectors;
the processing circuit is housed in an additional housing that is different from the housing of each wearable module included in the plurality of wearable modules; and
the processing circuit is communicatively coupled with the plurality of wearable modules by way of a wired or wireless communication link.

17. The optical measurement system of claim 16, wherein the additional housing is wearable by the user.

18. The optical measurement system of claim 1, wherein the wearable module assembly comprises a head-mountable component configured to be worn on a head of the user.

19. The optical measurement system of claim 1, wherein the target comprises a brain of the user.

20. The optical measurement system of claim 19, wherein:
the target comprises a particular functional region of the brain; and
the plurality of wearable modules are configured to entirely cover the particular functional region of the brain.

21. The optical measurement system of claim 1, wherein the wearable module assembly further comprises a pressing member configured to press the plurality of wearable modules toward the surface of the body of the user when the wearable module assembly is worn on the body of the user.

22. The optical measurement system of claim 1, wherein the wearable module assembly further comprises an auxiliary module configured to detect biological signals from the target by a modality that is different from a modality of the plurality of wearable modules.

23. The optical measurement system of claim 22, wherein the auxiliary module is physically and flexibly connected to the plurality of wearable modules by way of the connecting assembly.

24. A wearable module assembly for an optical measurement system, the wearable module assembly comprising:
a first wearable module comprising:
a first light source configured to emit a first light pulse toward a target within a body of a user;
a first housing that houses the first light source and the plurality of first detectors; and
a plurality of first detectors each positioned at a fixed distance from the first light source and each configured to detect a first set of photons included in the first light pulse after the first set of photons are scattered by the target;
a second wearable module comprising:
a second light source configured to emit a second light pulse toward the target; and
a plurality of second detectors each positioned at the fixed distance from the second light source and each configured to detect a second set of photons included in the second light pulse after the second set of photons are scattered by the target;

a second housing that houses the second light source and the plurality of second detectors;

wherein the first housing and the second housing have a substantially hexagonal surface that is substantially parallel to a surface of the body of the user when the wearable module assembly is worn by the user; and a connecting assembly that physically connects the first wearable module with the second wearable module, wherein the first wearable module and the second wearable module are connected edge-to-edge via a connector that directly connects at mutually-facing side surfaces of the first and second housings.

25. The optical measurement system of claim 24, wherein corners of the first wearable module and the second wearable module are rounded.

26. The optical measurement system of claim 24, wherein one or more of the first wearable module or the second wearable module is removable from the connecting assembly.

* * * * *